(12) United States Patent
Jackson et al.

(10) Patent No.: US 6,294,667 B1
(45) Date of Patent: Sep. 25, 2001

(54) ANALYSIS OF CARBOHYDRATES

(75) Inventors: Peter Jackson, Fulbourne; William Jonathan Cummins, Herts; Richard West, Uxbridge; John Anthony Smith; Mark Samuel Jonathan Briggs, both of Cardiff, all of (GB)

(73) Assignee: Amersham International PLC, Little Chalfont Bucks ( * ) Notice: Subject to any disclaimer, the term of this patent is extended or adjusted under 35 U.S.C. 154(b) by 0 days.

(21) Appl. No.: 09/284,046

(22) PCT Filed: Oct. 3, 1997

(86) PCT No.: PCT/GB97/02727

§ 371 Date: Jun. 10, 1999

§ 102(e) Date: Jun. 10, 1999

(87) PCT Pub. No.: WO98/15829

PCT Pub. Date: Apr. 16, 1998

(30) Foreign Application Priority Data

Oct. 7, 1996 (GB) .................................................. 9620881
Jul. 28, 1997 (EP) .................................................. 97305550

(51) Int. Cl.[7] .......................... C07H 1/06; G01N 27/26; G01N 27/447; G01N 33/58
(52) U.S. Cl. ........................ 536/127; 536/123; 536/25.4; 204/456; 204/459; 204/461; 204/548; 436/172
(58) Field of Search ................................... 204/456, 459, 204/548, 461; 436/94, 172; 548/427; 536/18.5, 25.4, 123, 127

(56) References Cited

U.S. PATENT DOCUMENTS

| 5,268,486 | 12/1993 | Waggoner et al. ............... 548/427 |
| 5,284,558 | * 2/1994 | Linhardt et al. ............... 204/182.8 |
| 5,453,505 | * 9/1995 | Lee et al. ............... 544/124 |
| 5,472,582 | * 12/1995 | Jackson ............... 204/180.1 |

FOREIGN PATENT DOCUMENTS

| 3912046 | 3/1990 | (DE) | ............................ C09B/62/002 |
| 0 233 053 | 8/1987 | (EP) | ............................ C12Q/1/68 |
| WO 88/10422 | 12/1988 | (WO) | ............................ G01N/27/26 |
| WO 91/05256 | 4/1991 | (WO) | ............................ G01N/33/52 |
| WO 91/11531 | 7/1992 | (WO) | ............................ G01N/27/26 |
| WO 93/02356 | 2/1993 | (WO) | ............................ G01N/33/00 |
| WO 96/00902 | 1/1996 | (WO) | ............................ G01N/33/58 |
| WO 96/04405 | 2/1996 | (WO) | ............................ C12Q/1/68 |
| WO 96/13552 | 5/1996 | (WO) | ............................ C09B/23/02 |

OTHER PUBLICATIONS

Hase, S. et al., "Analyses of Oligosaccharides by Tagging the Reducing End with a Flourescent Compound," *J. Biochem.*, 85(4):989–994 (1979).

Jackson, P. et al., "The use of polyacrylamide–gel electrophoresis for the high–resolution separation of reducing saccharides labelled with the fluorophore 8–aminonaphthalene–1,3,6–trisulphonic acid," *Biochem. J.*, 270:705–713 (1990).

Jackson, P., "Polyacrylamide Gel Electrophoresis of Reducing Saccharides Labeled with the Fluorophore 2–Aminoacridone: Subpicomolar Detection Using an Imaging System Based on a Cooled Charge–Coupled Device," *Analytical Biochemistry*, 196:238–244 (1991).

* cited by examiner

*Primary Examiner*—Marianne P. Allen
*Assistant Examiner*—Marjorie A Moran
(74) *Attorney, Agent, or Firm*—Marshall, O'Toole Gerstein, Murray & Borun

(57) ABSTRACT

The present invention discloses a method of separating or distinguishing carbohydrate substances. More particularly the method includes using fluorescent labeling reagents which have a positive charge when bound to a carbohydrate, involves separating the labeled carbohydrate substances, such as by performing electrophoresis to cause differential migration of different labeled carbohydrate substances, or by isoelectric focusing in a pH gradient. The fluorescent labeling reagents are preferably cyanine dyes.

13 Claims, 4 Drawing Sheets

ANALYSIS OF CARBOHYDRATES

This application is a national stage filing under 35 U.S.C. §371 of PCT/GB97/02727, filed Oct. 3, 1997.

FIELD OF THE INVENTION

This invention concerns the analysis of carbohydrates

BACKGROUND TO THE INVENTION

The publication by Wenn (Wenn, R. V. (1975) Biochem. J. 145, 281–285) discloses, inter alia, techniques for analysing carbohydrate structures or distinguishing or separating carbohydrate substances, involving labelling glycopeptides with a fluorescent labelling reagent, e.g. dansylcadaverine, and separating them by electrophoresis on a paper matrix (paper-electrophoresis) after application to that matrix. The fluorescent labelling reagent imparts a charge to the carbohydrates enabling their electrophoretic separation and it also enables the visualisation of the substances after the electrophoresis.

The publication by West (West, M. H. P., et al. (1984) Electrophoresis 3, 133–138) discloses a technique for the electrophoretic separation of charged substances of relatively low molecular weight, such as amino acids and their oligomers, involving applying the amino acids to an electrophoretic gel made of a polymer of acrylamide, that is a polyacrylamide gel, and separating the substances by the application of an electrical potential to the gel. This technique is known as PAGE. The publication by West also discloses that an electrophoretic gel matrix of relatively high concentration of polyacrylamide enables the separation of the amino acid leucine from its dimer, leucylleucine which in turn is separated from the homologous trimer, leucylleucylleucine and so on. In the publication by West the amino acids were rendered detectable by the use of amino acids that comprised radioisotopic atoms in their structures.

The publication of Weitzman et al. (Weitzman, S., et al. (1979) Anal. Biochem. 97,438–439.) discloses that carbohydrate substances of relatively low molecular weight can be separated by electrophoresis in a polyacrylamide gel when an electrophoretic buffer system that contains borate ions is used.

The publication by Poretz and Pieczenik (Poretz, R. D. and Pieczenik, G. (1981) Anal. Biochem. 115, 170–176) discloses the labelling with a fluorescent labelling reagent of glycopeptides and also discloses their separation after electrophoresis in a polyacrylamide gel and their detection by the incorporated fluorescent label.

The publication by Prakash and Vijay (Prakash, C. and Vijay, I. A. (1983) Anal. Biochem. 128, 41–46) discloses the labelling of carbohydrate substances with a fluorescent labelling reagent.

The publication by Towbin et al. (Towbin, H., et al. (1988) Anal. Biochem. 173, 1–9) discloses the labelling of carbohydrate substances with a chromophore.

The publication by Hase et al. (Hase, S., et al. (1978) J. Biochem. 85, 989–994) discloses the electrophoretic separation by paper electrophoresis in two dimensions of carbohydrate substances labelled with the fluorescent labelling reagent aminopyridine.

The publications by Jackson (Jackson P., (1990) Biochem. J, 270, 705–713 and Jackson, P. 1992) Anal. Biochem. 196, 238–244) and international publications No. WO88/10422, No. WO91/05256, No. WO93/02356, and No. WO92/11531, disclose, inter alia, techniques for analysing carbohydrate structures or distinguishing or separating carbohydrate substances involving applying carbohydrate substances to an electrophoretic gel to cause differential migration of different substances. The carbohydrate substances may be pre-labelled with a fluorescent labelling reagent, for example 8-aminonaphthalene-1,3,6-trisulphonic acid (known as ANTS for brevity) to impart a charge to the substances, thereby to enable electrophoretic separation, and to enable visualisation of the substances after running the gel. Visualisation may be effected by the naked eye but other means such as photography or electronic imaging may also be used.

The techniques described as examples in the patents which are cited above involve the use of negatively charged or uncharged fluorescent labelling reagents. The separations of fluorescently labelled carbohydrate substances that have been described so far show a relatively limited degree of separation of carbohydrate substances a significant proportion of which are not resolved from each other by the electrophoresis in a useful way. In particular this applies to the asparagine linked glycans that have been analysed as shown in the publication by Stack and Sullivan (Stack, R. J., and Sullivan, M. T. (1992) Glycobiology 2, 85–92). The invention described herein is a novel and innovative development that is related to the methods that are described in the papers and patents cited above.

BRIEF SUMMARY OF THE INVENTION

The subject of the invention is the separation of the fluorescently labelled carbohydrate substances, by virtue of their different charge-to-mass ratios or other factors, so as to enable a much larger number of different fluorescently labelled carbohydrate substances to be separated from each other electrophoretically than has been possible previously and thereby to facilitate their structural determination and their identification. The invention is aimed in particular, but not exclusively, at resolving carbohydrate substances that have been released from glycoproteins, proteoglycans and glycolipids. Some of the procedures that are described do not involve electrophoretic separation but are related to it and provide for additional analyses or identification of the carbohydrate substances.

Preferably the method for separating or distinguishing carbohydrate substances comprises labelling carbohydrate substances with a fluorescent labelling reagent comprising a naphthalene ring structure or other suitable fluorescent structure, having as a substituent a reactive group capable of reacting with a reducing sugar to bind thereto, also having at least one substituent, that may also be the reactive group, capable of carrying at least one positive charge which may exist on the fluorescently labelled carbohydrate substances and does not extinguish the fluorescence of the labelling reagent; applying the labelled substances to an electrophoretic gel, or other matrix used to support electrophoretic separations, and running the electrophoresis to cause differential migration of different substances. The labelling reagent may be attached to sites on the carbohydrate substances after release, if necessary, from an attached biomolecule. Alternatively, the biomolecule may be modified in known ways to enable incorporation of the labelling reagent. A carbohydrate substance may be labelled with a labelling reagent such as those indicated in Table 1 by incubating the substances with the labelling reagent. In the case of some labelling reagents, such as those reacting by way of an amino group, it is preferable to add a reducing agent (e.g. sodium cyanoborohydride). The sodium cyanoborohydride is conveniently in solution in dimethylsulphoxide or other suitable solvent known to those skilled in the art.

BRIEF DESCRIPTION OF THE DRAWINGS

FIG. 4 depicts fluorescent images recorded from the Molecular Fluorimager S1 of the separation of glycans NA4 and NGA4.

FIG. 5 depicts fluorescent images recorded from the Molecular Fluorimager S1 of the separation of glycans A1 and A2.

FIG. 6 depicts fluorescent images recorded from the Molecular Fluorimager S1 of the separation of neocarrahexaose oligosaccharide.

FIG. 7 depicts fluorescent images recorded from the Molecular Fluorimager S1 of the separation of a glycan library.

DETAILED DESCRIPTION OF THE INVENTION

Fluorescent Labelling

Figure 2:
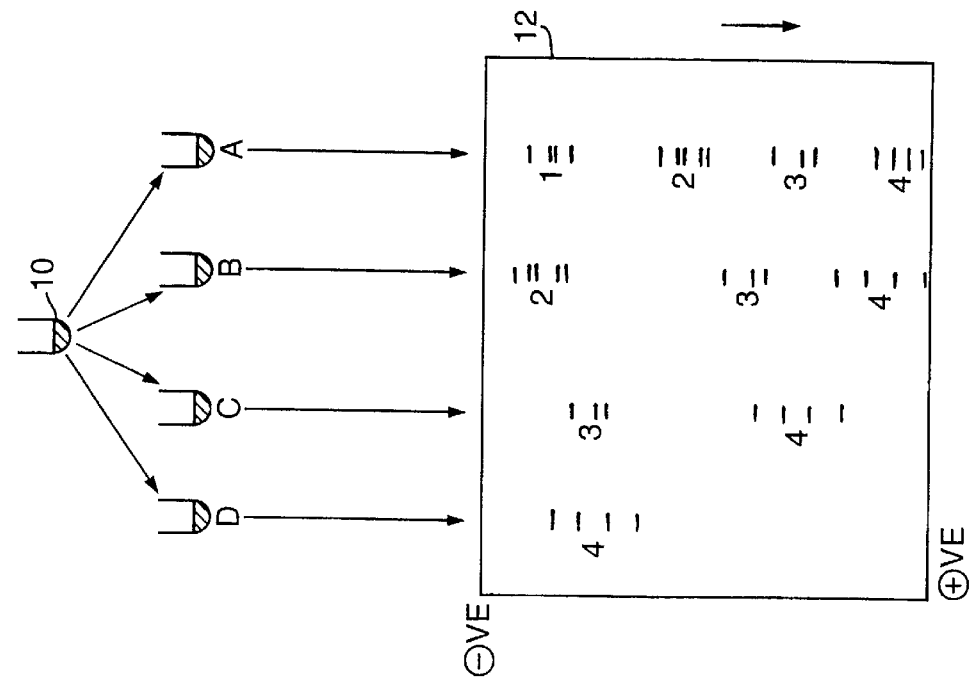
FIG. 2 is a diagram of a system for labelling and electrophoresis towards a positive electrode.

The fluorescent labelling reagent comprises a structure which may be selected for example from the following: naphthalene; anthracene; phenanthrene; pyrene; acridine; indole; benzoxazole; quinoline; isatoic anhydride; 1,8-napthalimide; 2,3-naphthalimide; 5-phenyl4-pyridyl-2-oxazole; coumarin; bimane; 6-N-(7-nitrobenz-2-oxa-1,3-diazol-4-yl) amine; 4,4-difluoro5,7-dimethyl4-bora-3a,4a-diaza-s-indacene; ethidium chloride; propidium dichloride; fluorescein; resorufin; Nile Blue A; dihydrotetramethylrosamine; dihydro-X-rosamine; benzimidazole; pyridine; and cyanine dyes. The carbon atoms that may be substituted on the ring structures will be known to those skilled in the art. One or more substituent groups may also be carried on the labelling reagent which do not react with carbohydrates and cannot carry a charge and do not extinguish the fluorescence. Such a group or groups may have the effect of modifying various characteristics of the labelling reagent, including the following: fluorescence properties, charge, reactive properties of other substituent groups such as the reactive group, physical properties such as solubility etc. Possible non-reactive substituents include halogens, aliphatic groups, acetyl groups, methoxy groups etc. Other suitable groups will be apparent to those skilled in the art. Such a substituent or substituents may be attached to any available carbon of the naphthalene or other ring structures, directly or indirectly through a spacer or linker group.

The currently preferred reactive groups capable of reacting with a reactive reducing carbohydrate are either a primary amino group (—$NH_2$) or a hydrazino group (—NH—$NH_2$) or an aminoxy group (—$ONH_2$) but other groups such as a secondary amino group (—NHR) or the pyrazolone group may alternatively be used. Further possible groups will be apparent to those skilled in the art.

The reactive group may be attached to any of carbons 1 to 8 of the naphthalene or to appropriate carbon atoms of other suitable fluorescent ring structures, or to nitrogen atoms in the case of the cyanine dyes. The reactive group may be attached directly to a carbon atom of the naphthalene or other ring structure, or may be attached indirectly via a linker or spacer group such as one or a series of linked aliphatic groups (e.g. methylene groups). For convenience this linker is called the reactive-linker. In addition, the reactive group, which may be situated at any position in the linker molecule, not necessarily at one end, may be capable of carrying a positive charge after the carbohydrate labelling procedure. It is desirable to include only one such reactive group so that only one carbohydrate molecule will bind to each molecule of labelling reagent.

Additional groups, other than the one that is involved in the labelling of the carbohydrates, that can react with carbohydrates, such as the primary amino group or secondary amino group, may comprise in part the structure of the fluorescent labelling reagent in a protected, masked, or derivatised state during the labelling procedure. For some procedures it is desirable to have as the means of protecting, masking or derivatising the reactive group and a method that allows the protecting, masking or derivatising to be reversed or removed. Such protected groups may be attached to the fluorescent labelling reagent ring structure or the reactive linker or any non-reactive linker.

The chemical group or groups comprising the linker or spacer that is attached to the reactive group (the reactive linker), but which are not themselves reactive with carbohydrate substances under conditions in which the defined reactive group is reactive, may be of any size or structure and the linker may contain either none or one or more groups capable of carrying a positive charge. The linker may therefore carry either none or one or more positive charges other than any which might exist on the reactive group. Any substituent group on the labelling reagent capable of carrying a charge may be present initially in the form of the basic uncharged form or as a salt such as the chloride salt and which ionises under appropriate conditions to form the positively charged form of the group.

In one embodiment of the labelling reagent it is preferable that no group capable of carrying a positive charge exists except that which may be carried by the reactive group after the labelling procedure. In another embodiment of the labelling reagent it is preferable that there is present a group or groups each capable of carrying a positive charge, that do not react with the carbohydrate, each individual group being attached to an available carbon atom of the naphthalene ring or other suitable fluorescent ring structure either directly or indirectly via a linker or spacer group that does not contain a group that is capable of reacting with a carbohydrate. For convenience this linker is called a non-reactive linker in order to distinguish it from that described above which contains a group capable of reacting with carbohydrates. The chemical group or groups comprising a non-reactive linker may be of any size or structure. The substituent groups that are each capable of carrying a positive charge may initially be present in the form of the basic uncharged form or as a salt, such as the chloride salt, and which ionises under appropriate conditions to form the positively charged form of the group. In any population of molecules of the fluorescent labelling reagent that are capable of carrying a charge some proportion may be uncharged and some may be singly or multiply charged the proportions depending on their structures and the conditions in which the molecules exist. Any number of groups each carrying a positive charge may be attached either directly or indirectly to the fluorescent ring structure consistent with maintaining the useful properties of its structure. A non-reactive linker may carry more than one group capable of carrying a positive charge and may therefore be capable of carrying more than one positive charge if desired.

The currently preferred substituent groups which are capable of carrying a positive charge but which do not react with the carbohydrate are the tertiary amino group (—$NR_1R_2$), the secondary amino group (—$NHR_1$), the quaternary ammonium group (—$N^+R_1R_2R_3X^-$) the guanidinium group (—NH(NH=)$CNH_2$), the imidazole group and the pyridinium group. Further possible groups will be apparent to those skilled in the art.

The fluorescent labelling reagent may also be comprised of a chemical group or groups each capable of carrying a negative charge (e.g. sulphate or sulphonate), in addition to any other substituent group or groups that may be present, either attached directly to the naphthalene ring or other suitable fluorescent ring structure through a linker which may is be either the reactive linker or a non-reactive linker. It is preferable that whatever the structure of the fluorescent labelling reagent the effect of the labelling of the carbohydrate substance shall be to confer a net positive charge on to the fluorescently labelled carbohydrate. The net positive charge that is conferred exists at the pH of the electrophoresis and may vary in degree during the electrophoresis for instance if the pH of the electrophoretic buffer changes. The net positive charge that is conferred to the carbohydrate substances by the labelling procedure may be numerically greater than, smaller than or equal to any charge, positive or negative, that may exist on the carbohydrate substances before the labelling procedure. It is preferable that any charge that is capable of existing on the carbohydrate substance before the fluorescent labelling procedure shall be capable of existing there afterwards. The resulting overall charge on the labelled carbohydrate substance will have an effect on its electrophoretic properties Preferred examples of fluorescent dyes that may be modified chemically to enable them to be used as fluorescent labelling reagents for carbohydrates are the Cyanine dyes. Cyanine dyes are a group of fluorescent substances that are related in their chemical structure. Cyanine dyes are described in U.S. Pat. Nos. 5,268,486 and 5,486,616. The basic structure of cyanine dyes has a +1 overall charge e.g.

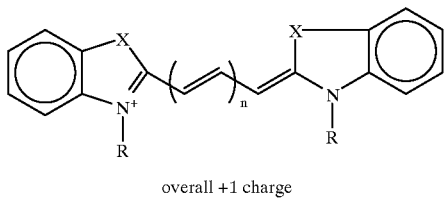

overall +1 charge where n is 1–3. Dyes with n=1 are Cy3 dyes. Dyes with n=2 are Cy5 dyes. Many variations of this basic dye structures are described in the aforesaid U.S. Patents.

Cyanine dyes useful in the method of the present invention have the structure (1)

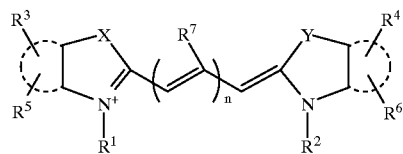

the cyanine dye having an overall positive charge greater than +1 and having at least one reactive or functional group, wherein the dotted lines represent the carbon atoms necessary for a one ring or a two or three fused ring system with 5 or 6 carbon atoms in each ring and $R^3$, $R^4$, $R^5$ and $R^8$ attached to the rings, X and Y are independently selected from O, S and $CR_2^8$, where $R^8$ is $C_1$–$C_4$ alkyl, n is 1, 2 or 3, at least one of $R^1$, $R^2$, $R^3$, $R^4$, $R^5$, $R^6$ and $R^7$ comprises a reactive or a functional group, at least one of $R^1$, $R^2$, $R^3$, $R^4$, $R^5$, $R^6$ and $R^7$ incorporates one to five positively charged nitrogen or phosphorus or sulphur atoms, any remaining $R^3$, $R^4$, $R^5$ and $R^6$ is independently selected from H, $SO_3^-$, Cl, Br, $OR^9$ and $SR^9$, where $R^9$ is $C_1$–$C_{10}$ alkyl or aryl or aralkyl, any remaining $R^1$ and $R^2$ is independently selected from $C_1$–$C_{10}$ alkyl or aryl or aralkyl either unsubstituted or substituted by $SO_3^-$, any remaining $R^7$ is selected from H and $C_1$–$C_{10}$ alkyl or aryl or aralkyl either unsubstituted or substituted by $SO_3^-$.

These cyanine dyes are mostly new compounds and are described and claimed as such in EP 97305550.2 filed Jul. 23, 1997, the entire disclosure of which is incorporated by reference herein. A chemical strategy for making these dyes is provided below.

According to this invention each member of the group of Cyanine dyes may be modified chemically so that each different Cyanine dye has incorporated a linker that can react with and bind to carbohydrates that have an aldehydic reducing group available for the reaction. This linker is called the reactive linker. It is preferred that only one reactive linker is incorporated into each Cyanine dye molecule. The Cyanine dyes that have been modified to incorporate a carbohydrate reactive linker may also be modified in addition by the incorporation of a non-reactive linker that is distinct and separate from the reactive linker. The non-reactive linker may be bound to the Cyanine dye molecule by any chemical or physical means at any suitable position in the Cyanine dye molecule. The non-reactive linker has the property of carrying one or more positive ionic charges. In one example this non-reactive linker has a chemical structure that enables it to carry a single positive ionic charge. In another example the non-reactive linker may have a different structure that enables it to carry two positive charges. It is also preferred that there exists a group of structurally different non-reactive linkers each member of which group may carry a specific number of positive ionic charges that is different from that carried by any other member of the group. Any non-reactive linker, whatever its structure or charge may be incorporated into and therefore modify any Cyanine dye molecule. The number of positive charges that may be carried by any single non-reactive linker may be any number. Any Cyanine dye that has a reactive linker may also be used to label carbohydrates without the addition of the non-reactive linker. Any Cyanine dye that has a reactive linker shall be capable of labelling carbohydrate substances irrespective of the structure of the non-reactive linker.

It is preferred that in some cases a Cyanine dye shall be modified by the incorporation of an additional chemical group, for instance a sulphonate group, that is distinct and separate from the non-reactive and the reactive linkers, that can alter the properties of the Cyanine dye so as to enhance it usefulness in this invention for instance by increasing its solubility in selected solvents or solutions. Such an additional group may alter the overall charge on the Cyanine dye but such an additional group shall not alter the applicability of the dye in the invention.

Each member of the group of Cyanine dyes is distinguished from any other member by its different chemical structure. Each of the Cyanine dyes has specific maximum fluorescence emission wavelengths that is strongly influenced by the chemical structure of the chain of carbon atoms that join the two ring structures. Often the longer the carbon linker chain the longer the maximum fluorescence emission wavelength. In one example of the invention a Cyanine dye that has a carbon chain joining the two ring structures constituted by a specific number of carbon atoms shall also have incorporated a non-reactive linker that can carry one positive ionic charge. In another example of the invention a Cyanine dye with a different specific maximum fluorescence emission wavelength will have the property of carrying two positive ionic charges. It is preferred that there is a group of Cyanine dyes each of which has a different chemical structure, each of which has a different fluorescence maximum emission wavelength and each of which has a different non-reactive linker that carries a specific number of positive ionic charges. Thus the maximum emission wavelength of any one Cyanine dye with a defined structure is correlated with the number of positive ionic charges that the Cyanine dye structure can carry. Thus it is possible to determine the number of positive charges carried by a specific Cyanine dye structure by measuring the maximum wavelength of its fluorescence emission.

The Electrophoretic Procedure

Electrophoretic separation may be carried out in a generally conventional manner, using techniques known to those skilled in the art. It is preferred that polyacrylamide gel electrophoresis is used but other electrophoretic methods such as capillary zone electrophoresis may also be used either in free solution or in a gel or other supporting or interactive matrix.

In the case of polyacrylamide electrophoresis the electrophoretic gel preferably comprises a relatively dense polyacrylamide gel, having a concentration in the range 5% (w/v) to 60% (w/v), preferably 15% (w/v) to 40% (w/v).

The electrophoretic gel or matrix may be alternatively a copolymer of acrylamide and one or more other substances that confer advantageous properties either on the making or manufacture or handling of the gel, or on the electrophoretic running of the gel or the analysis or viewing of the carbohydrate substances which are separated in the gel. An example of a substance which may be copolymerised together with acrylamide to form an electrophoretic gel is polyethyleneglycol having any suitable molecular weight range. The ratio of the polyethylene glycol to the acrylamide used to form the gel may be any suitable to a confer the advantageous properties.

The electrophoretic gel or matrix may be formed of polyacrylamide and may contain one or more other substances which do not polymerise or copolymerise with the acrylamide but are present in the gel during its preparation and remain there during the electrophoresis. The purpose of these substances is to confer advantageous properties either on the making or manufacture or handling of the gel, or on the electrophoretic running of the gel or the separation of the substances being analysed or viewing of the carbohydrate substances which are separated in the gel. Examples of such substances are dimethylsulphoxide and urea.

Substances other than polyacrylamide can be used as the support matrix for the electrophoresis, for example paper.

The gel or matrix or any incorporated substances may be either of uniform concentration, or in the form of a gradient.

The polyacrylamide gel is preferably cross-linked, e.g. with N, N' methylenebisacrylamide.

For good resolution and sensitivity the electrophoresis is preferably run using a stacking buffer system (also known as moving boundary electrophoresis, multiphasic zone electrophoresis and other names), using techniques for working with protein and DNA fragments, e.g. as described in the book "Gel Electrophoresis of Proteins: a practical approach" edited by B. D. Harnes and D. Rickwood, published by IRL Press.

In one embodiment of the electrophoretic method the stacking buffer system is designed to enable the electrophoresis in the gel of positively charged substances. The pH of any of the buffers which may be in the gel or gels or in the electrode compartments are such that the pH of the resolving gel is in the range pH1 to 13. One such system that enables the separation of positively charged substances in a polyacrylamide gel is described in a publication by Thomas and Hodes (Thomas, J. M. and Hodes, M. E. (1981) Anal.Biochem. 118, 194–196. Other effective buffer systems are described in the publication by Chrambach and Jovin (Chrambach, A. and Jovin, T. M. (1983) Electrophoresis 4, 190–204) and others may be known to those skilled in the art.

After the electrophoresis the labelled carbohydrates substances, when illuminated with light of a suitable wavelength (e.g. ultra-violet), may be visible with the naked eye in some cases although better sensitivity may be obtained by imaging with a cooled charge coupled device (CCD). Use of a CCD also has the advantage of giving readily quantitative results and high sensitivity. Further, CCDs can be used to view the gel while the electrophoresis is proceeding.

It is preferred to use a cooled 2-D CCD, having a low noise silicon chip operating at −25° C. or a higher temperature. Other digital imaging systems capable of detecting light at low levels are known to those skilled in the art.

Application of a Group of Positively Charged Fluorescent Labelling Reagents When Used in Conjunction The fluorescent labelling reagents that are described previously in this invention (above) can be used as described as follows: It is preferred that more than one labelling reagent are used together as a group to obtain a better separation of the constituents of a mixture of carbohydrates and to yield more information about carbohydrate structures than is possible when one labelling reagent is used singly. Any number of reagents greater than one may constitute the group if so desired. By way of example a group of labelling reagents (which for convenience is called an analytical fluorophore group) can consist of four different but possibly related labelling reagents. The members of such a group of four labelling reagents have the following properties. One of the members of the group of reagents is capable of conferring a single positive charge to the labelled carbohydrate substances. Another is capable of conferring two positive charges to the carbohydrate substances, another is capable of conferring three positive charges and another is capable of conferring four positive charges. The charged state of each labelled carbohydrate substance exists after the labelling reaction. The positive charges exist at the pH of the electrophoresis but the net mean charge on all the molecules of any one structure of labelled carbohydrate substance being analysed may vary in degree during the electrophoresis if the pH or other property of the electrophoretic buffer system varies during the electrophoresis. This net mean charge on any labelled carbohydrate substance may therefore be integral or partial. The net mean charge, whether integral or partial, on all the molecules of any one fluorescently labelled carbohydrate substance being analysed relative to any other remains approximately the same during the electrophoretic procedure. In one format of the method it is preferred that the electrophoresis of the labelled carbohydrates substances that are being analysed proceed in the gel towards a cathodic (i.e. negatively charged) electrode (cathode).

Each labelling reagent is used separately to label a carbohydrate substance or a mixture of carbohydrate substances. Thus by way of example a single mixture of carbohydrate substances that is to be analysed by electrophoresis is divided into four approximately equal portions and each is labelled by one only of the four labelling reagents that have been chosen to constitute the analytical fluorophore group. For a group of four different labelling reagents there result four differently labelled portions of each single carbohydrate sample that is to be analysed. Each labelled portion is analysed by application to the same single electrophoretic gel. Each portion being applied in an individual manner, that is, the separately labelled portions are not mixed together and are electrophoresed separately but simultaneously in the same gel preferably in different lanes. The electrophoresis of the labelled carbohydrates that are being analysed proceeds towards a cationic (i.e. negatively charged) electrode. The result of this analysis is shown diagrammatically in FIG. 1 and described as follows:

A mixture of carbohydrate substances (10) to be analysed has been divided into four portions. A first portion has been labelled with a fluorescent labelling reagent A which confers one positive charge per molecule. A second portion has been labelled with a fluorescent labelling reagent B which confers two positive charges per molecule. A third portion has been labelled with a fluorescent labelling reagent C which confers three positive charges per molecule. A fourth portion has been labelled is with a fluorescent labelling reagent D which confers four positive charges per molecule. Each portion of labelled carbohydrate substances has been applied to the top positive edge of an electrophoresis gel (12). Electrophoresis towards a negative electrode has caused bands to move downwards (in the figure) through the gel.

Each line marked as — represents a fluorescently labelled carbohydrate substances shown as a band on the gel. Bands marked 1 have less than 1 negative charge per molecule. Bands marked 2 have less than 2 negative charges per molecule. Bands marked 3 have less than 3 negative charges per molecule. Bands marked 4 have less than 4 negative charges per molecule.

Molecules of carbohydrate substances that have no charge before they are labelled with fluorescent labelling reagent will be capable of being electrophoresed after labelling with any of the fluorescent labelling reagents that impart any positive charge, or a partial positive charge, to the carbohydrate derivatives that result from the labelling.

Carbohydrate molecules that have a single or a partial (less than unity) negative charge, for instance those having a single sialic acid residue per molecule, will be capable of being electrophoresed towards a cationic (i.e. negatively charged) electrode after labelling with any fluorescent labelling reagent that imparts more than one positive charge to the carbohydrate derivatives that result from the labelling.

Carbohydrate molecules that have two or less negative charges will be capable of being electrophoresed towards a cationic (i.e. negatively charged) electrode after labelling with any fluorescent labelling ro reagent that imparts more than two positive charges to the carbohydrate derivatives that result from the labelling.

Carbohydrate molecules that have three or less negative charges will be capable of being electrophoresed towards a cationic (i.e. negatively charged) electrode after labelling with any fluorescent labelling reagent that imparts more than three positive charges to the carbohydrate derivatives that result from the labelling.

Carbohydrate molecules that have four or less negative charges will be capable of being electrophoresed towards a cationic (i.e. negatively charged) electrode after labelling with any fluorescent labelling reagent that imparts more than four positive charges to the carbohydrate derivatives that result from the labelling.

In each sample any labelled carbohydrate substance that has a net negative charge, owing to the presence of negative charges on the carbohydrate substance, will not electrophorese into the gel and will therefore not be visible in the gel.

In some cases the net mean charge per molecule on a number of fluorescent labelling reagent molecules before labelling or on a fluorescently labelled carbohydrate substance molecules after labelling may not be integral. The average charge will depend on the nature of the fluorescent labelling reagent, the carbohydrate substance and the conditions in which they exist (e.g. the pH of the solution).

Each different fluorescent labelling reagent may be used in conjunction with any other suitable fluorescent labelling reagent.

The Resulting Patterns of Electrophoretic Separation Towards a Cathode

The overall result of the electrophoresis described above is to facilitate the separation of all the carbohydrates substances present and in particular those that carry different charges. In each lane of the electrophoretic gel carbohydrate substances of a particular size that have the greater positive charge will migrate more rapidly and be separated from those having less charge. By way of example it is instructive to consider one lane of an electrophoretic gel that has applied to it a mixture of carbohydrate substances labelled with one fluorescent labelling reagent. In the common case, when a mixture being analysed consists of numerous different carbohydrate substances, the derivatives of those carbohydrate substances of approximately the same size that, before labelling, carried no charge on each molecule are separated substantially from those with one charge which in turn are separated from those with two charges and so on. Simultaneously, labelled carbohydrate substances carrying the same charge but with different electrophoretic mobilities will also be separated from each other.

Those carbohydrate substances that are capable of carrying no negative charge before labelling can be considered to belong to one group. Those carbohydrate substances that are capable of carrying one negative charge before labelling can be considered to belong to a second group. Those carbohydrate substances that are capable of carrying two negative charges before labelling can be considered to belong to a third group and so on. The number of such groups that can appear in a lane on the gel depends on the number of positive charges that are carried by the fluorescently labelled carbohydrate. For example a fluorescent labelling reagent that confers four positive charges as a result of the labelling procedure will enable labelled carbohydrate substances that have any number less than four negative charges to move into the gel in the lane to which has been applied a mixture containing such components. Members of a group of labelled carbohydrate substances with the greater net positive charge will tend to electrophorese more rapidly than those in a charge-group with lesser net positive charge. Within each charge-group separation between members will also occur. There may be a degree of overlap between the various groups of molecules. Thus some of the lower mobility singly charged molecules may have mobilities similar to those with two charges. However the separation of most members of each charge group from members of other groups is achieved.

In the analysis of carbohydrate substances obtained from natural sources it is common for there to be present carbohydrate substances having different negative charges (i.e. belonging to different charge groups) and therefore the number of components in each charge group is equal to or in most cases less than the total number of components in any complete mixture that is analysed. The number of components of a complete mixture that will appear in any one part of the electrophoretic gel is thus diminished by virtue of labelling portions of the carbohydrate mixture separately with different fluorescent labelling reagents, each carrying a different number of charges, and applying the fluorescently labelled carbohydrate substances in separate lanes of the gel. The number of carbohydrate components of a mixture that can enter the gel is decreased progressively from gel lane to gel lane as the number of positive charges conferred by each different fluorescent labelling reagent drops until in the lane containing the reagent that confers only one positive charge only those carbohydrates with zero charge or less than one negative charge will appear on the gel. The result of this separation is to simplify greatly the separation pattern of fluorescent bands of fluorescently labelled carbohydrate substances in each sample lane of the electrophoresis gel. The complexity of the pattern of separation in any one lane is simplified compared with methods described in the introduction in which all components of a mixture are electrophoresed in one lane, for instance when using ANTS as the labelling reagent. Thus the likelihood that each carbohydrate substance component of a mixture that is being electrophoresed will have a similar electrophoretic mobility to any other is diminished significantly.

An Additional Electrophoresis Towards a Positive Electrode in Order to Obtain Additional Information It may be preferable to obtain additional information by running the electrophoresis in an alternative format of the method so that the labelled carbohydrates that have a net negative charge move through the gel or matrix towards an anionic (positively charged) electrode (anode). That is, a portion of each sample of fluorescently labelled carbohydrate a substance that has been labelled with any one of the fluorescent labelling reagents, that constitute the analytical fluorophore group, is electrophoresed in an electrophoretic system of opposite polarity to that described previously. The electrophoretic buffer system applicable to this separation is a stacking system. One example of such a system is that described by Laemmli (Laemmli, U. K. (1970) Nature 227, 680–685). In such a system carbohydrates that have been labelled with a fluorescent labelling reagent, such that the average net charge on each labelled carbohydrate molecule is negative, will migrate electrophoretically towards the anode (positively charged electrode). In the case of a fluorescent labelling reagent that confers no positive charge to a labelled carbohydrate substance then carbohydrates that carry any negative charge will migrate electrophoretically towards the cathode but those with no negative charges will not migrate to the anode but will either remain at the origin if their derivative has no charge or will migrate towards the cathode and away from the gel if their derivative carries a net positive charge. Thus the fluorescently labelled carbohydrate derivatives of uncharged and singly charged carbohydrate molecules will not enter the gel when labelled with a fluorescent labelling reagent which confers a single positive charge to them.

When carbohydrate molecules are labelled with a fluorescent labelling reagent that confers one positive charge to a carbohydrate substance only those carbohydrates that have more than one negative charge will migrate electrophoretically towards the positive electrode. An analogous situation occurs with fluorescent labelling reagents conferring two or more positive charges. The components having the greater positive charge will tend to migrate more rapidly than those having lesser.

The resulting patterns of separation will further reduce the possibility that any two components of a mixture of carbohydrate substances that are being analysed will coincide in position. A diagram showing the envisaged system is shown in FIG. 2.

Figure 1:
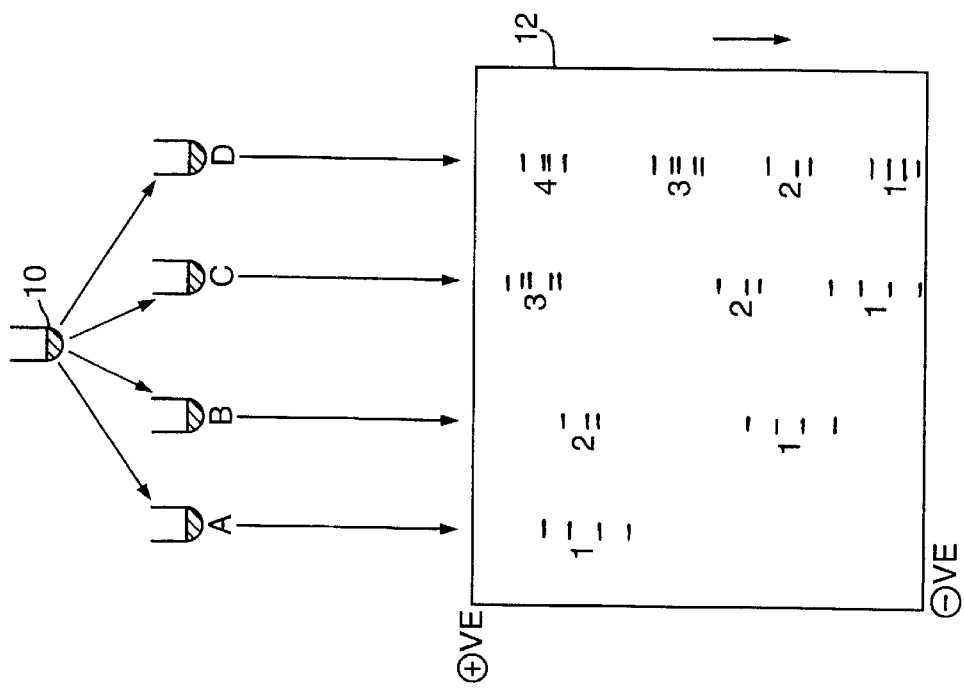
FIG. 1 is a diagram of a system for labelling and electrophoresis towards a negative electrode.

As in FIG. 1, each line marked as — represents a fluorescently labelled carbohydrate substance shown as a band on the gel. Bands marked 1 have more than 1 negative charge per molecule. Bands marked 2 have more than 2 negative charges per molecule. Bands marked 3 have more than 3 negative charges per molecule. Bands marked 4 have more than 4 negative charges per molecule.

Fluorescent labelling reagent A confers 1 positive charge per molecule. Fluorescent labelling reagent B confers 2 positive charges per molecule. Fluorescent labelling reagent C confers 3 positive charges per molecule. Fluorescent labelling reagent D confers 4 positive charges per molecule.

Summary of a Comprehensive Analysis

A single comprehensive analysis of a mixture of carbohydrates will consist of dividing the sample into parts labelling each part with a different fluorescent labelling reagent dividing each labelled part into two and electrophoresing one part in a gel electrophoresis system towards a positively charged electrode (for the separation and analysis of anionic derivatives) and electrophoresing the other part in a gel electrophoresis system towards a negatively charged electrode (for the analysis of cationic derivatives). The probability of resolving any one labelled carbohydrate substance from all others that might be present in a mixture is therefore enhanced.

That is, the effect will be to reduce, in comparison with other procedures, the possibility of coelectrophoresis or approximate coelectrophoresis of the derivatives of different carbohydrate substances. This effect will make possible the comparison of the electrophoretic mobilities of carbohydrate substances whose identity is unknown with those whose identity is known thus facilitating the identification of the unknown carbohydrates. Since the rate of migration of substances undergoing electrophoresis varies with the size (molecular weight) and structure of the substances the invention may thus be used to obtain information on the size and shape of the carbohydrate substances, and by comparing results with known standards it may be possible partly or fully to characterise an unknown carbohydrate substance. One use of the invention may be in elucidating carbohydrate structures by cleaving them into smaller fragments by specific glycosidase enzymes and identifying the resulting fragments by the electrophoretic system described herein.

Comparison of the mobilities of the known and unknown carbohydrate substances can be achieved either by electrophoresis of the relevant samples side by side in adjacent gel lanes or by coelectrophoresis. In the case of non-planar electrophoretic systems such as capillary zone electrophoresis then comparison of mobilities can be carried out by accurate measurement of the mobilities. The invention described herein may therefore be used as a means of accumulating electrophoretic mobility data that can be used to identify certain carbohydrate substances known as glycans by reference to a Glycan Electrophoretic Mobility Index (also known as GEMI) as described in the publication by Jackson (Jackson, P. (1994) Anal. Biochem. 216, 243–252).

A Further Application of the Method Involving Separation in a Single Gel Lane or a Column or Tube or Capillary Tube When the wavelength of the emitted light from the different fluorescent labelling reagents, that are being used to label one sample of carbohydrate substances that are to be analysed, differs from one fluorescent labelling reagent to the next then electrophoresis of all the samples in the same lane simultaneously may be preferable. In the latter case the carbohydrate substances that are labelled with the different fluorescent labelling reagents may be distinguished from each other by excitation of the fluorescent substances with light of a wavelength that matches their absorbance and by the use of suitable filters to distinguish the wavelengths of the light emitted from each of the fluorophores. A preferred example of an analytical fluorophore group that can be used as described here in this invention are those Cyanine dyes that have chemical structures in which the maximum fluorescence emission wavelength is correlated with a specific positive ionic charge that is carried by that specific structure. Typically the members of the analytical fluorophore group shall have overall positive ionic charges in the range from one to five. The advantage of being able to distinguish the different Cyanine dyes by their different maximum fluorescent wavelengths and therefore their net positive ionic charges is that the electrophoretic procedure is simplified as it enables the separations to take place and be analysed in a single column or tube. Thus in the case of capillary electrophoresis and other electrophoretic separation methods that involve separations in a single gel lane, or a column, or tube, or capillary tube then it may be preferable to use the procedure of mixing the parts of the carbohydrate sample after they have been labelled with the different fluorescent labelling reagents and separating them simultaneously in a single gel lane, or a column, or tube, or capillary tube and distinguishing the separated components that are labelled with a different fluorescent labelling reagent by using exciting light of a wavelength and emission filters of a wavelength that permits any one fluorescent labelling reagent to be distinguished from any other. The exciting light may be generated conventionally or by a laser or lasers operating at a suitable wavelength(s). The emitted light may be detected by a suitable spectrofluorimeter that are available commercially or other light sensitive or detecting apparatus that is known to those skilled in the art.

A Further Embodiment of the Invention Involving Separation by Isoelectrc Focusing According to the present invention described here the structural analysis and identification of carbohydrate substances may be further facilitated by a novel development of the methods described in the patent: Jackson, P. (1993) Analysis of Carbohydrates. Patent Publication No. WO92/11531 which discloses a method for the separation by two dimensional polyacrylamide gel electrophoresis of acidic carbohydrate substances labelled at the reducing end with the fluorescent labelling reagent 2-aminoacridone.

According to the present invention described here, carbohydrate substances that contain acidic groups before labelling, that is carbohydrate substances that are capable of carrying either a mean partial, or one, or more negative ionic charges, for instance through the presence of sialic acid or sulphate or phosphate groups, or other acidic groups known to those skilled in the art, may be labelled with a fluorescent labelling reagent that confers a overall partial positive charge or one or more positive charges per molecule to the labelled carbohydrate substances. The charge conferred by the fluorescent labelling reagent may be carried on any suitable part of the molecule of the fluorescent labelling reagent. Fluorescent labelling reagents and the methods and techniques described in other parts of this invention can be applied to this part of the invention where appropriate.

As a result of the fluorophore labelling of the carbohydrate substances there can occur on the fluorescently labelled carbohydrate substances both positive and negative ionic charges that may cause the labelled carbohydrate substance to be zwitterionic and exist in a state in which they have no overall charge. The condition of having no overall charge can be brought about by adjusting the pH of an aqueous solution in which the labelled carbohydrate substance is present. The pH at which it has no overall charge is known as the isoelectric point of the labelled carbohydrate substance. Such a labelled carbohydrate substance can be separated from other carbohydrate substances labelled with the same or other fluorescent labelling reagents by the method of isoelectric focusing (IEF) in a suitable pH gradient that can be generated either by the use of carrier ampholytes or by an immobiiised pH gradient (IPG) using, for instance, Immobiline reagents that can be obtained from the company Pharmacia-Biotech. In another embodiment of the invention the carrier ampholytes may be incorporated into the immobilised pH gradient so as to improve the separation of the labelled carbohydrate substances that are being analysed.

The effect of using Immobiline reagents is to enable a greater reproducibility and resolution in the separations of the derivatised carbohydrates and to allow a wider range of the pH gradient in particular to more basic pHs than is usually possible with conventional IEF that uses carrier ampholytes alone.

The matrix used for the IEF is typically polyacrylamide gel but may be other permeable substances, such as agarose gel, known to those skilled in the art. In the case of IPG the matrix to which the immobilised ampholytes are attached is usually polyacrylamide but other suitable permeable substances such as agarose gel may be used. For the purposes of convenient handling and/or stability the gel or matrix in which the separation takes place may be attached to a supportive backing such as glass or plastic or other polymer by methods known to those skilled in the art. The IEF may also be carried out in free solution in tubes or other suitable vessels including capillary tubes or in tubes or capillary tubes that are filled with a suitable permeable matrix or gel such as polyacrylamide gel. The separation of the fluorophore labelled carbohydrate substances may also be carried out in an apparatus that is designed initially to enable the electrophoresis in a polyacrylamide gel, by methods well known to those skilled in the art, of nucleic acids that may in some cases be labelled with a fluorescent dye. Such an apparatus is applicable to the determination of the sequence structure of deoxyribonucleic acid (DNA) but may be modified as appropriate for the electrophoresis of fluorophore labelled carbohydrate substances.

Any suitable fluorescent labelling reagent may be used to label the acidic carbohydrate substances so as to enable the separation by IEF. Preferred examples of fluorescent substances that may be used as labelling reagents for carbohydrates are the Cyanine dyes after they have been suitably chemically modified, as described previously in this invention. The fluorescent labelling reagent shall have the property that its fluorescence is readily detectable when illuminated by a light of any suitable wavelength after the IEF, in a gel or other matrix used, or after focusing in a tube or capillary tube, at any pH generated by the pH gradient. Separations that are carried out in any form of tube can be visualised by the use of a suitable detector by methods known to those skilled in the art.

Thus in practice a mixture of carbohydrate substances that are to be analysed are labelled with the fluorescent labelling reagent and then subjected to IEF so that the different carbohydrate substances in the original mixture are separated according to their isoelectric points after they have been labelled. According to this invention different labelled acidic carbohydrate substances that are distinguished one from another, at least in part, by having different numbers of negative ionically charged groups, for instance when comprised of different numbers of sialic acid residues or other negatively charged groups, will have different isoelectric points and will focus at different pHs. The different labelled carbohydrate substances, for instance those that occur in a mixture obtained from a biological source, can therefore be separated from each other. Isomeric carbohydrate substances having the same number of negative ionically charged groups but having different structures may also be separated from each other by virtue of their differing isoelectric points since their isoelectric points may be determined in part by the structural positions and the subsequent interactions between ionically charged groups on the same molecule after labelling with a fluorescent labelling reagent.

The physical basis of the IEF separation is different from the electrophoresis described previously in this invention and will result in a different pattern of separation and thus increase the probability that any one component of the mixture of carbohydrates can be separated from any other component.

In an additional embodiment of the invention the sample of carbohydrate substances that is to be analysed is labelled separately by a several different fluorescent labelling reagents, that together constitute an analytical fluorophore group as described in previously in this invention, each member of the group having a different overall charge that is conferred to the carbohydrate substance by the labelling. Thus by way of example, a single mixture of carbohydrate substances that is to be analysed by IEF is divided into four approximately equal portions and each is labelled by one only of the four labelling reagents that have been chosen to constitute the analytical fluorophore group. For a group of four different labelling reagents there results four differently labelled portions of each single carbohydrate sample that is to be analysed. Each labelled portion is analysed by application to the same single IEF gel. Each portion being applied in an individual manner, that is, the separately labelled portions are not mixed together and are focused separately but simultaneously in the same gel preferably in different lanes. The separation pattern is viewed after the IEF gel or other matrix containing the separation pattern is illuminated by light of a suitable wavelength.

In one preferred example of a group of fluorescent labelling reagents that constitute an analytical fluorophore group, that may be used to label carbohydrate substances and enable their separation by IEF, are the Cyanine dyes, that incorporate a suitable carbohydrate reactive group, that have been described previously in this invention.

The result of this separation will be to move the carbohydrate substances that have been labelled with different labelling reagents to different parts of the pH gradient depending on the charge on the labelling reagent used. This will cause the charges that arise from different carbohydrate substances to change in a way that is dependent on their structure and so increase the probability that a different separation pattern for any one mixture of carbohydrate substances will be produced for each labelling reagent. The result of procedure will be to increase the potential for achieving separation of any one carbohydrate component from any other in the original mixture from any other.

Figure 3:
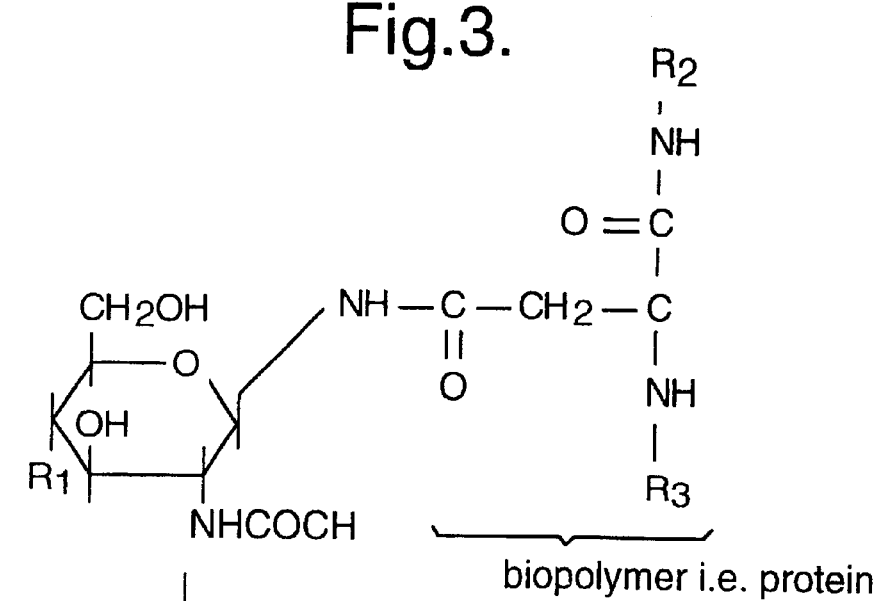
FIG. 3 is a scheme showing the reaction of hydrazine with a carbohydrate substance that is linked to a biopolymer.
Figure 3:
Figure 3:
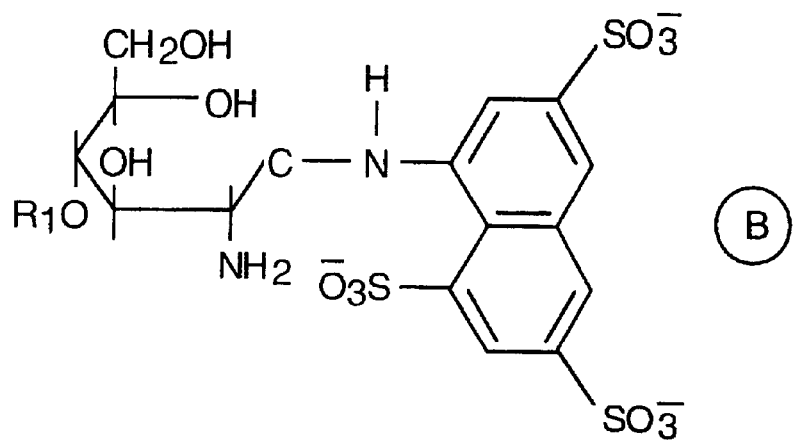

Analysis of Carbohydrate Substance After Release or Cleavage or Treatment with Hydrazine In another embodiment of this invention it is desirable to provide a means for the separation of carbohydrate substances that have been cleaved from glycoprotein or glycolipid substances or other glycoconjugates by the action of hydrazine. It is also desirable to provide a means for the separation of carbohydrate substances, that do not comprise a glyconjugate such as glycans and glycosaminoglycans (GAGS), that have been treated with hydrazine so as to alter their structure. Hydrazine may be used for the cleavage or release or treatment of carbohydrate substances according to methods that have been described previously in numerous publications and are well known to those skilled on the art. The cleaved or released or treated carbohydrate substances are obtained in a form that is a derivative known as a hydrazone. During the hydrazinolysis cleavage or release reaction, and also in the case of the treatment of carbohydrate substances, that are not conjugated with other biomolecules (for example those substances known as glycans), with hydrazine, the acetyl groups of the acetylated aminosaccharide residues (such as a hexosamine residue), that are commonly constituent parts of many carbohydrate substances, are cleaved from the amino groups leaving free primary aliphatic amino groups on the cleaved carbohydrate substance. A diagrammatic representation of a typical hydrazine cleaved carbohydrate substance structure is shown in FIG. 3.

In this figure, the hydrazine cleaved carbohydrate substance is shown as cleaved carbohydrate product A. Product A is labelled with a fluorescent reagent such as ANTS to give product B after reduction with sodium cyanoborohydride. Other labelling reagents such as amino fluorescein may be used instead of ANTS.

According to the present invention the carbohydrate substances that have been cleaved or released or treated with hydrazine are labelled with a fluorescent labelling reagent that is capable of being negatively ionically charged preferably by the fluorescent labelling reagent being in part comprised by a group or groups that are capable of being negatively ionically charged. Examples of such groups are the carboxyl group (—COOH), the sulphate group (—$SO_4$) and the phosphate group (—$PO_4$) other suitable groups are known to those skilled in the art. A list of suitable fluorescent labelling reagents is shown in Table 2. A method for fluorescently labelling carbohydrate substances, that have been cleaved from their glycoconjugate by hydrazine, is described in the publication by Jackson (Jackson, P. (1993) Methods in Enzymology 230, 250–265).

A fluorescent labelling reagent that is comprised of a chemical group or groups capable of carrying any negative charge or charges whether partial or integral will confer that charge onto the labelled carbohydrate substances. The labelled carbohydrate substances are therefore capable of carrying both positive charges by virtue of their amino groups that have been revealed by the action of hydrazine and negative charges derived from the fluorescent labelling reagent. The labelled carbohydrate substances therefore have zwitterionic properties and can exist in a state in which they have no overall charge and can be separated by IEF as described previously in this invention.

In an additional embodiment of the present invention the carbohydrate substances that have been cleaved or released or treated with hydrazine are labelled with a fluorescent labelling reagent that is capable of being positively ionically charged and conferring this positive ionic charge to the labelled carbohydrate substance as described previously in this invention. The labelled carbohydrate substances are therefore capable of carrying both positive charges by virtue of their amino groups that have been revealed by the action of hydrazine and positive charges derived from and conferred by the fluorescent labelling reagent and also other negative charges derived from any negatively charged group that may exist on the carbohydrate substances and which are not eliminated by the treatment with hydrazine, such as sialic acid or other chemical groups known to those skilled in the art. The labelled carbohydrate substances therefore may have zwitterionic properties and can exist in a state in which they have no overall charge and may be separated by IEF as described previously in this invention.

In an additional embodiment of the present invention the carbohydrate substance hydrazone is labelled with a fluorescent labelling reagent that has no ionic charge and confers no charge to the labelled carbohydrate substances. The labelled carbohydrate substances are therefore capable of carrying both positive charges by virtue of their amino groups that have been revealed by the action of hydrazine and negative charges derived from any negatively charged group that may exist on the carbohydrate substances and which are not eliminated by the treatment with hydrazine, such as sialic acid or other chemical groups known to those skilled in the art. The labelled carbohydrate substances therefore may have zwitterionic properties and can exist in a state in which they have no overall charge and may be separated by IEF.

In one embodiment of this invention an analytical fluorophore group may consist of one or more fluorescent labelling reagents that can confer one or more positive charges to the carbohydrate substance together with one or more fluorescent labelling reagent that can confer one or more negative charges to the carbohydrate substance together with one or more fluorescent labelling reagent that confer no charges to the carbohydrate substance.

In one embodiment of the invention it is preferable to view the fluorescently labelled carbohydrate substances after they have been separated in a single dimensional IEF when they are illuminated by light-of a suitable wavelength. Patterns of separation can be recorded by any conventional means such as photography or electronic imaging.

The separation of carbohydrate substances labelled with different fluorescent labelling reagents that have different spectral properties may be separated simultaneously in the same lane of a gel or in a tube or capillary tube that is being used for the IEF. A specific fluorescent label may be detected individually by illuminating with light of a suitable wavelength and detecting emitted light of specific wavelengths by appropriate optical filtration that enable the different fluorophores to be distinguished one from another.

The result of the separation by IEF is to enable a mixture of carbohydrate substances, that have been subject to treatment with hydrazine and then labelled with the fluorescent labelling reagent, to be separated according to their isoelectric points after they have been labelled. The physical basis of this separation is different to electrophoresis and will result in a different pattern of separation and thus increase the probability that any one component of the mixture of carbohydrates can be separated from any other component.

Any carbohydrate substances that have been cleaved or released or treated with hydrazine may be labelled, if desired, with any fluorescent labelling reagent described previously in this invention and analysed by any electrophoretic method described previously in this invention.

The methods described in this invention may also reveal information on the structure of the carbohydrate substances by enabling the number of charges on the structure to be determined. The methods are particularly suited to the separation of carbohydrate substances cleaved from glycoconjugates by hydrazinolysis since it makes use of the presence of amino groups on the carbohydrate substances generated by deacetylation during the hydrazinolysis and simultaneously avoids the usual procedure of reacetylation of the carbohydrate substance amino groups before further analysis.

Two-Dimensional Separations

In an additional embodiment of the invention, after separation by IEF that uses carrier ampholytes or in an immobilised pH gradient or a combination of the two, the separated labelled carbohydrate substances may be further separated in a second dimension perpendicular to the IEF by applying the matrix, that contains the isoelectric separation, to a polyacrylamide gel and subjecting the focused labelled carbohydrate substances to electrophoresis. According to this invention described here different electrophoretic buffer systems may be used to enable the electrophoresis in the gel used for the second dimension of fluorescently labelled carbohydrate substances that carry an overall positive charge as described previously in this invention. In the case of analysis by two-dimensions the fluorescent labelling reagent need only be fluorescent after the second dimensional electrophoresis has been run. In one preferred example of the invention any Cyanine dye, that is used for the fluorescent labelling of the carbohydrate substances, may be used for the two-dimensional separations.

The result of the two-dimensional separation is to increase the probability that separation of different labelled carbohydrate substances will be achieved.

Chemical Strategy

This section shows the chemistry envisaged in making cyanine dyes having positive charges from 2 to 6. Each numbered paragraph starts with a general picture of a cyanine dye shown as a rectangle, having a single positive charge shown as + within a circle. To two corners of the rectangle are attached curved lines which may comprise at least one positive charge and/or at least one functional or reactive group Q or Q'; these curved lines correspond to $R^1$, $R^2$, $R^3$, $R^4$, $R^5$, $R^6$ and $R^7$, most usually $R^1$ and $R^2$, in the structure (1) shown above.

1.

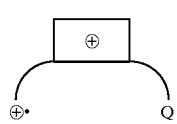
+ 2 DYES

The dye carries an inherent +1 charge. A second + charge is located on a chain attached to one of the dye N atoms. A functional or reactive group Q terminates a chain attached to another dye atom e.g. the other N atom.
Examples:

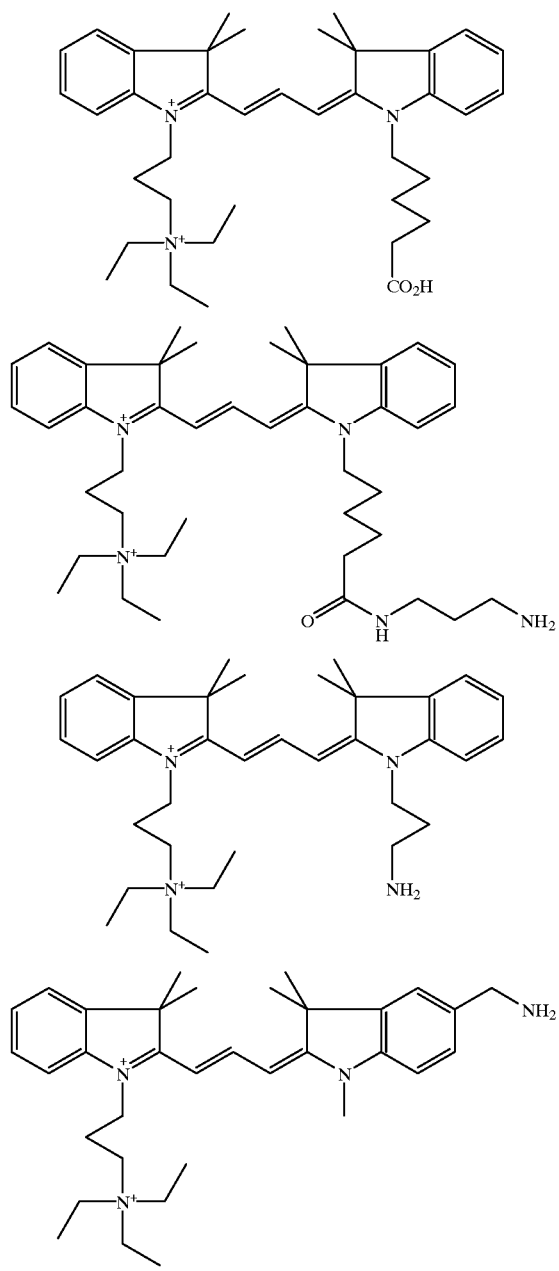

2.

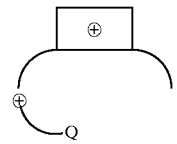

The dye carries an inherent +1 charge. A second + charge is located on a chain attached to one of the dye N atoms. A functional or reactive group Q terminates the same chain.

Example:

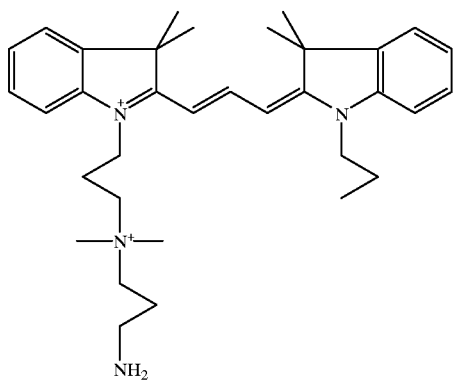

Synthesis of +2 intermediate:

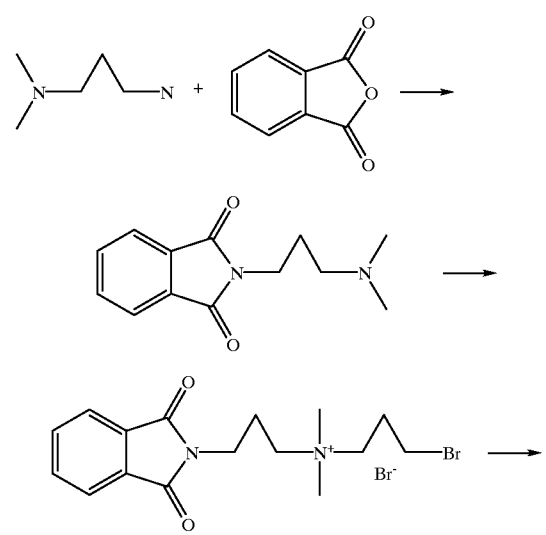

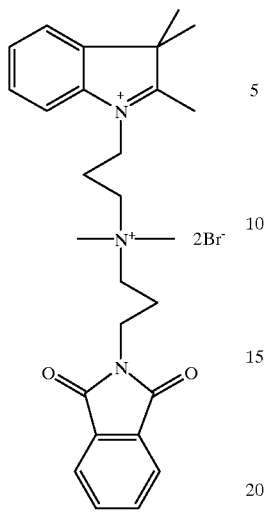

This intermediate is used to make the protected dye. The phthalimide is removed by hydrolysis in hydrochloric acid to give the amine dye.

3.

A +1 monoreactive dye is extended with a linker, which itself contains the second + charge. A possible example is as follows:

This avoids the requirement for +2 indolinium intermediates. The synthesis is also more like a convergent type. It could be adapted to "bolt on" a linker containing any number of + charges.

Projected synthesis of +1 linker:

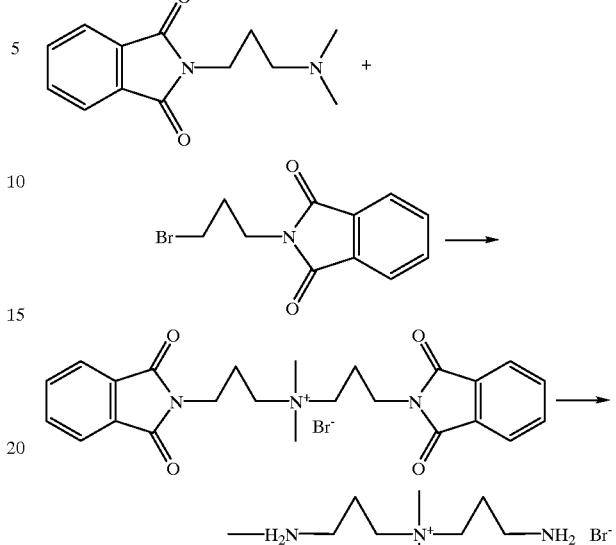

+3 Dyes

These examples are analogous to those for +2 dyes.

1.

The dye carries an inherent +1 charge. The two extra + charges are located on a chain attached to one of the dye N atoms. A functional or reactive group Q terminates a chain attached to another dye atom e.g. the other N atom.

Examples:

-continued

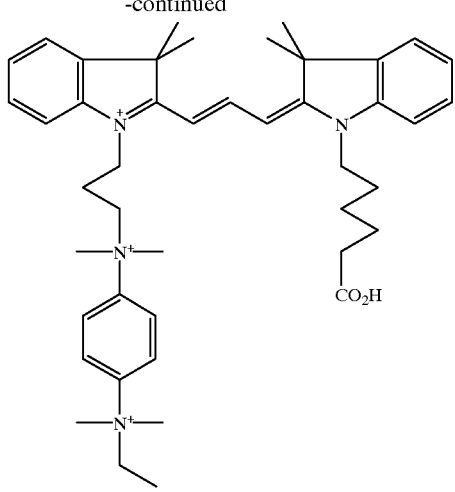

The dye carries an inherent +1 charge. There is one extra + charge on each chain attached to the dye N atoms. A functional or reactive group Q terminates one of these chains.
Example:

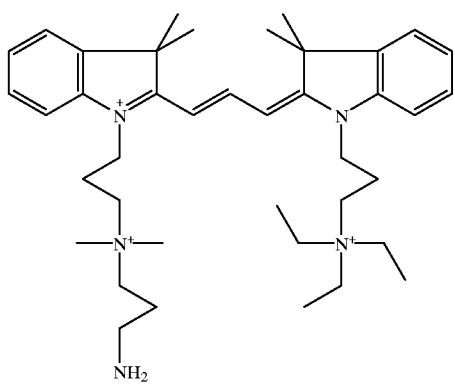

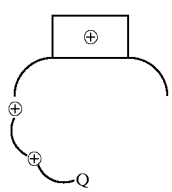

The dye carries an inherent + charge. The other two + charges are both on one chain off a dye N atom; this chain also includes a functional or reactive group Q. This requires a +3 charged intermediate containing a functional or reactive group.
Examples:

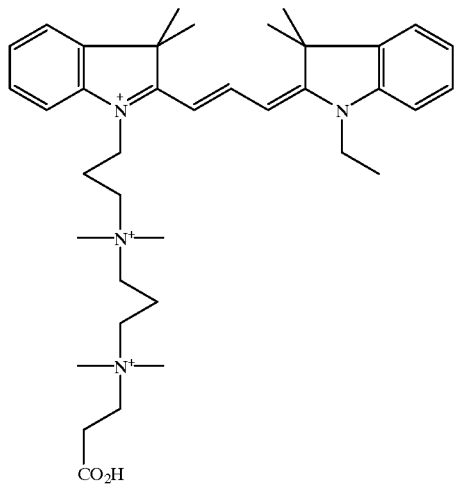

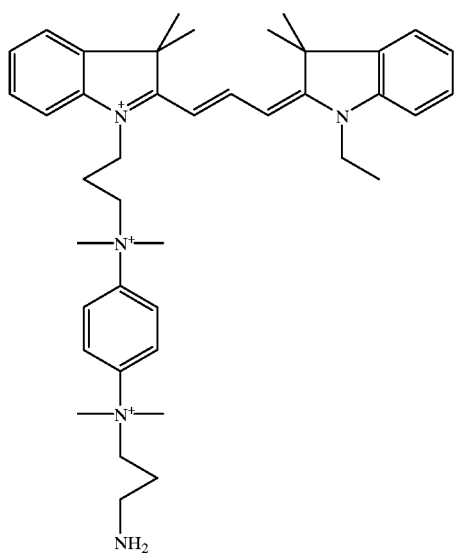

4. Conversion of a +2 dye to a +3 dye by addition of a +1 linker:

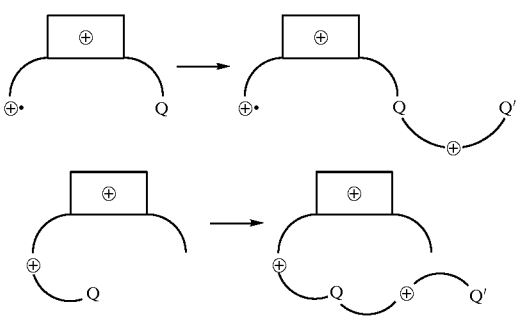

Example:
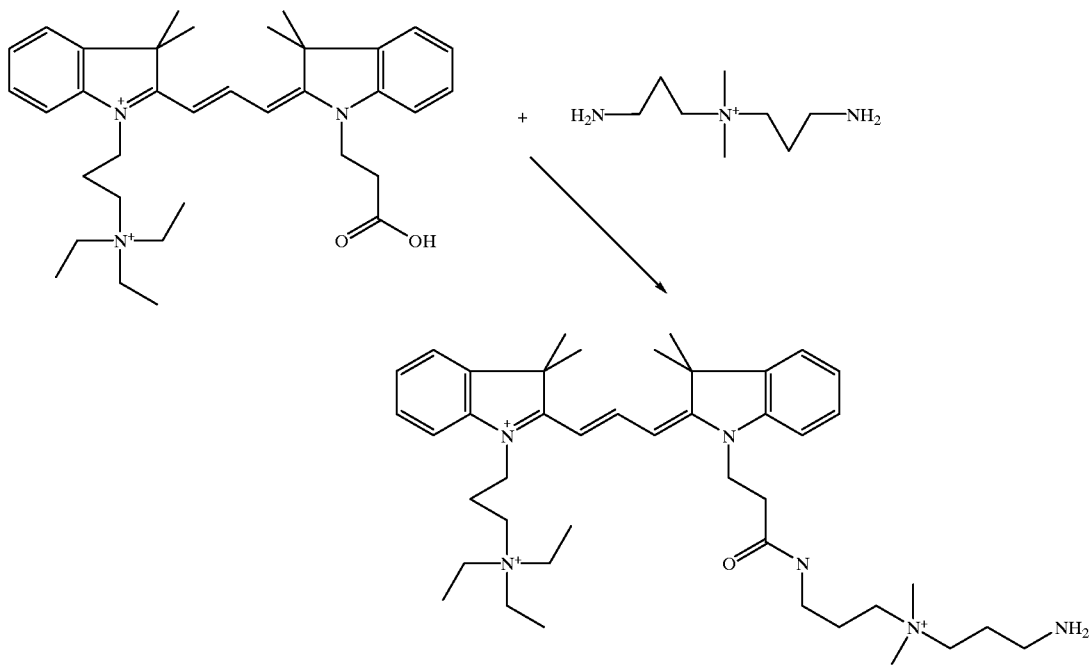
5. Conversion of a +1 dye to a +3 dye by addition of a +2 linker.
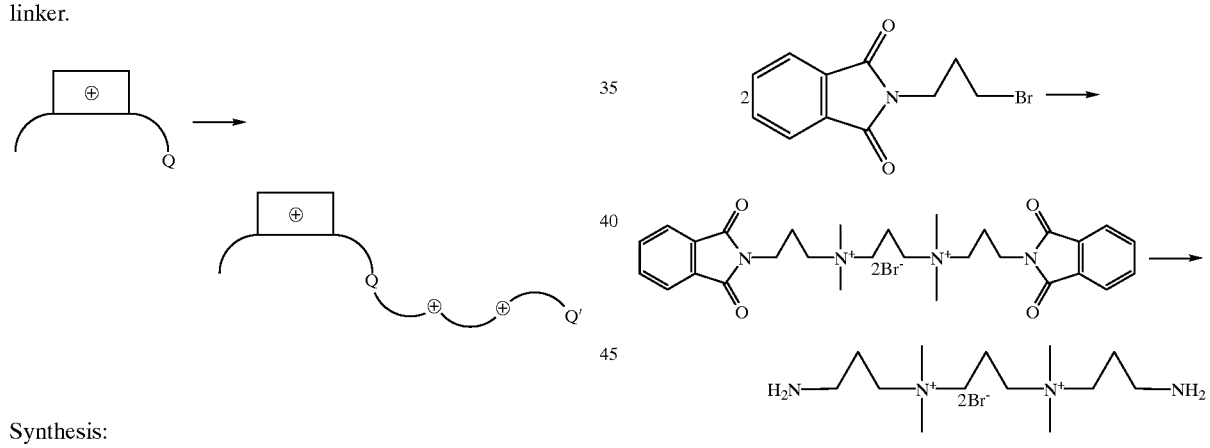
Synthesis:
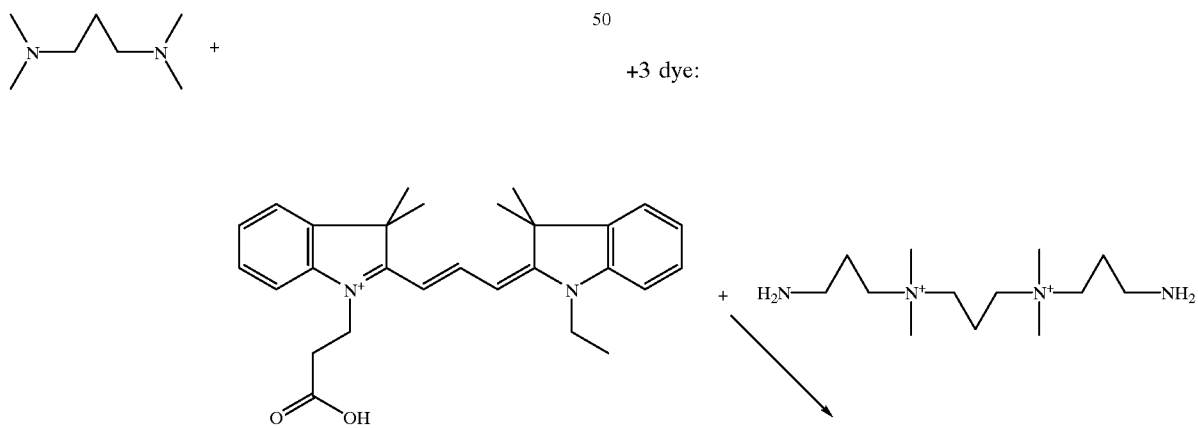
+3 dye:

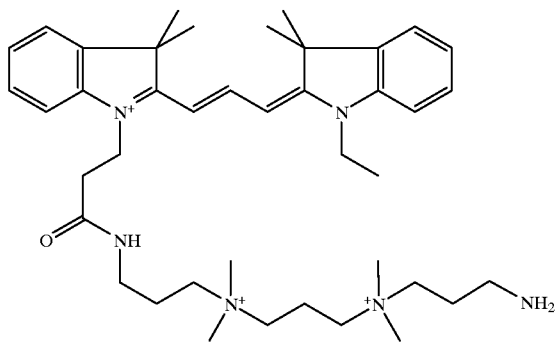
+4 Dyes
1. Conversion of a +2 dye to a +4 dye by addition of a +2 linker:
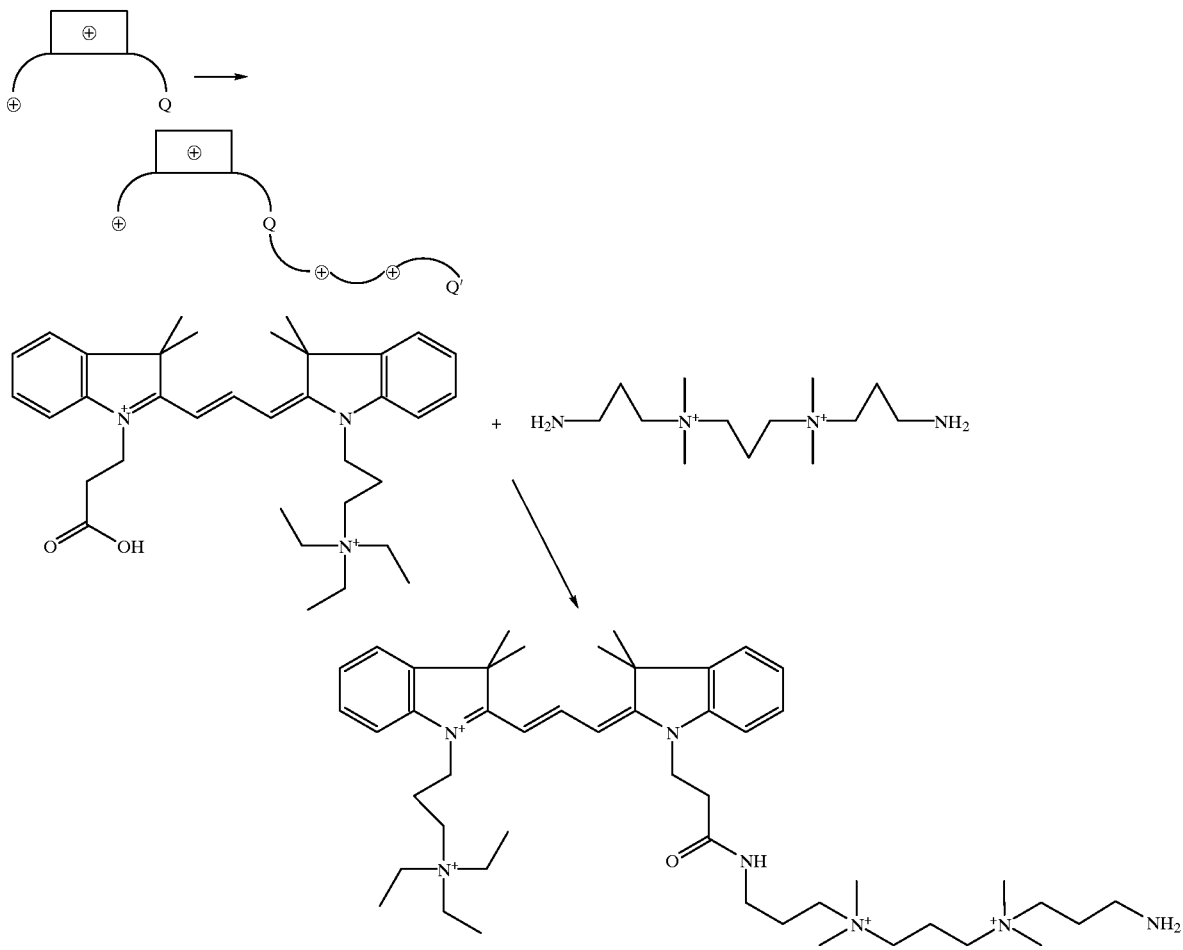

2. Conversion of a +1 dye to a +4 dye by addition of a +3 linker:
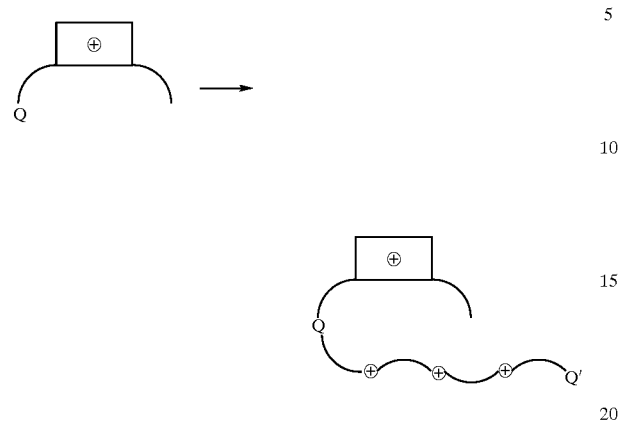
Example:
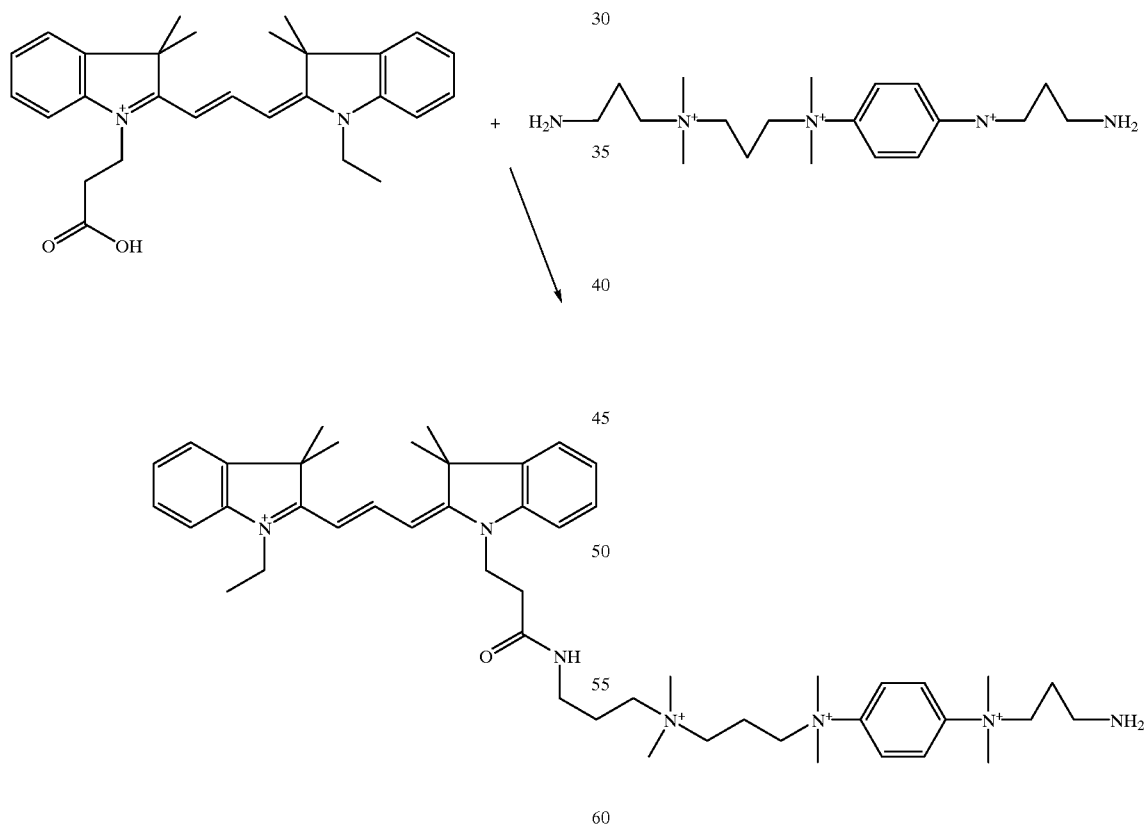
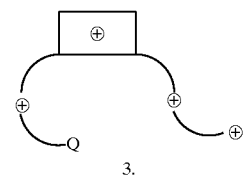
3.

Requires a +2 intermediate with a reactive group and a +3 intermediate.
Example:
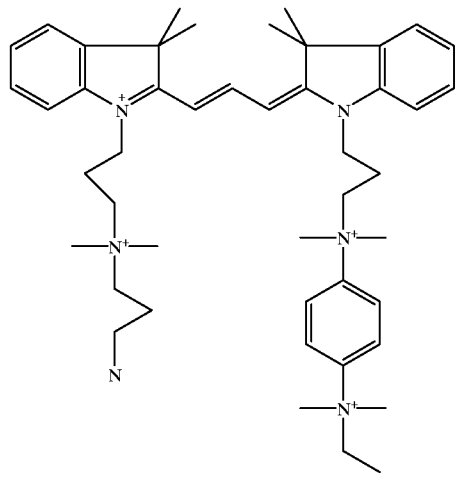
+5 and +6 Dyes
1. Conversion of a +2 dye to a +5 dye by addition of a +3 linker:
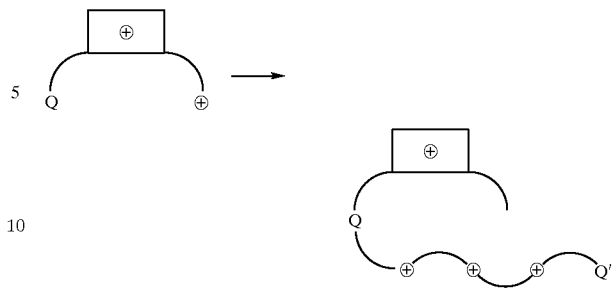
2. Conversion of a +1 dye to a +5 dye by addition of a +4 linker:
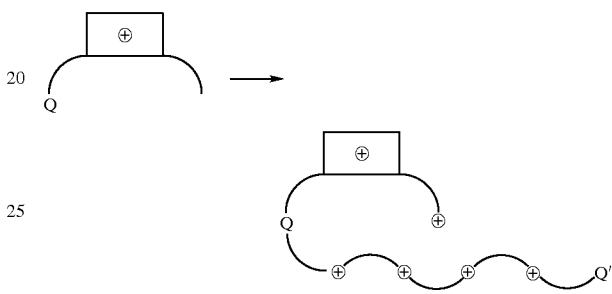
The +4 linker:
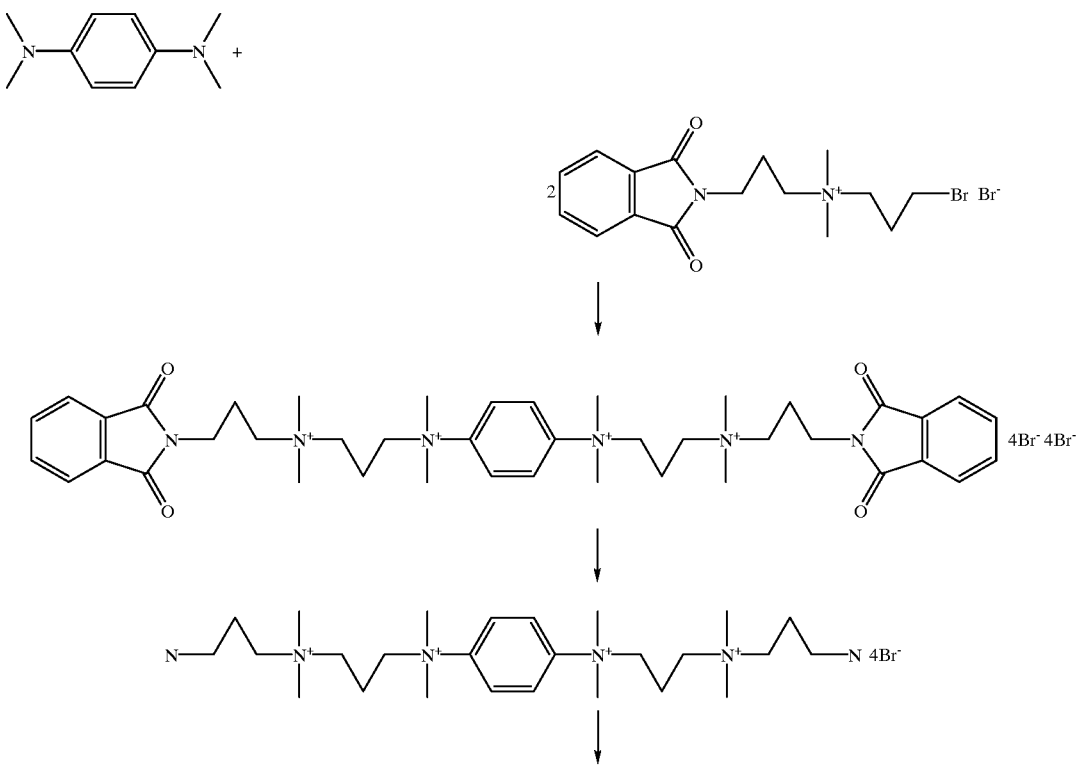

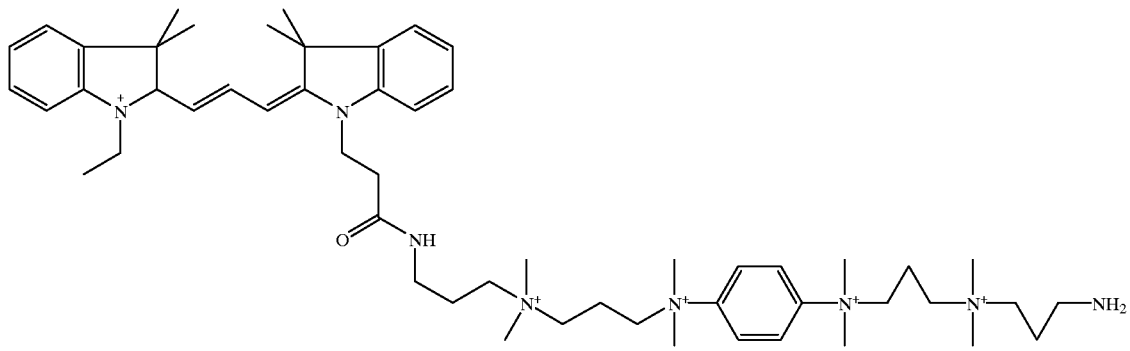
3. Conversion of a +2 dye to a +6 dye by addition of a +4 linker:
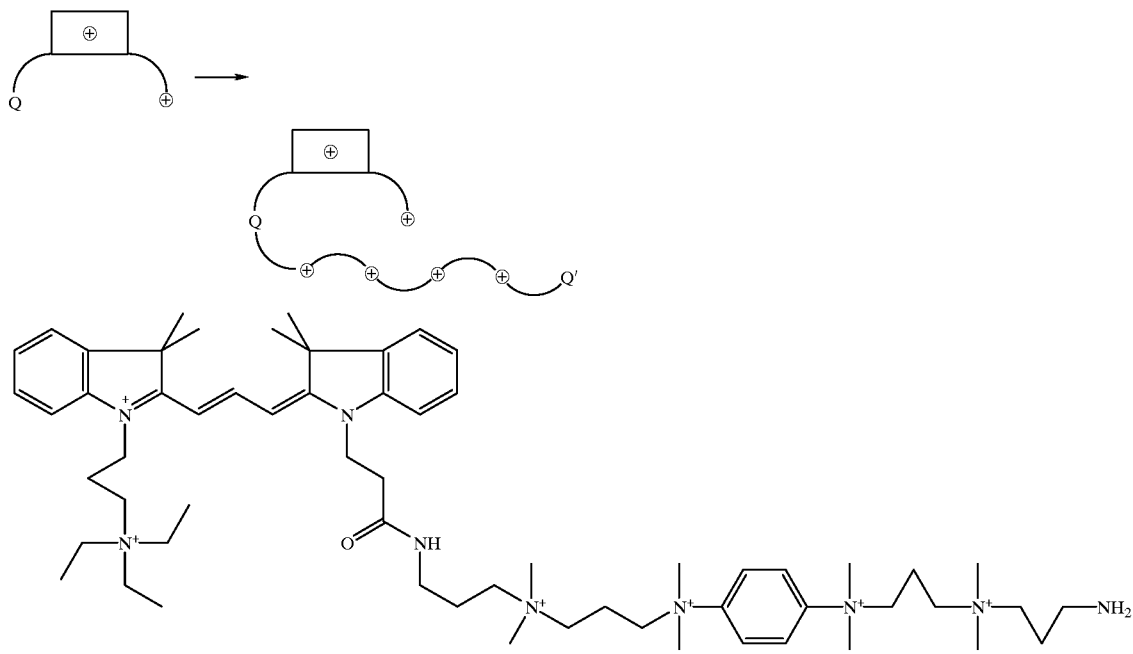
Linker Chains Based on Poly-Lysine
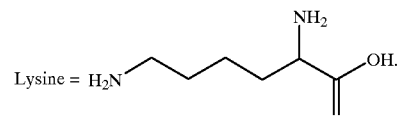
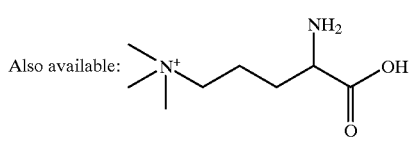
Construct oligomers on a solid support and couple to +1 dyes to give n+ dyes:
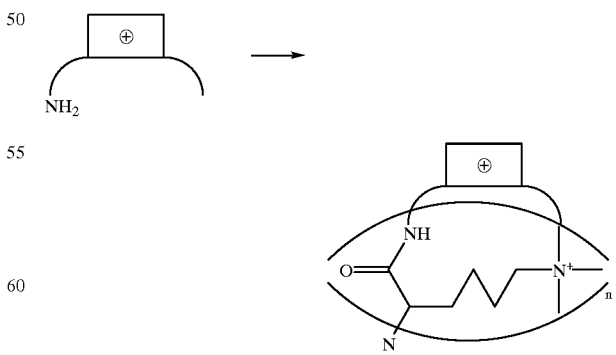
(n+1) charged dye where n is 1–5 or 6

EXAMPLES

Introduction

Carbohydrate chains or oligosaccharides derived from proteins are referred to as glycans. Glycans are either neutral or negatively (−) charged depending on the presence or absence of sialic acid groups or other groups conferring a negative charge. Each sample of glycan can be labelled with the range of neutral or charged fluorescent dyes e.g. (+1, +2, +3, +4). In these examples, a neutral +1 and +2 Cy3 hydrazide have been used to label the free reducing end of an oligosaccharide. The labelled glycan sample has been divided into two aliquots and each aliquot separated by electrophoresis towards the positive or the negative electrode. The net charge on the glycan sample is altered when a positively charged fluorescent dye has been used. In these examples, the original charge on the glycan has been determined by noting the presence or absence of fluorescent bands. The position of these bands is affected by their different net mass to charge ratios.

Dye Preparation

A. Net Zero Charged 'Cy-3' Hydrazide

Preparation of Parent Dye

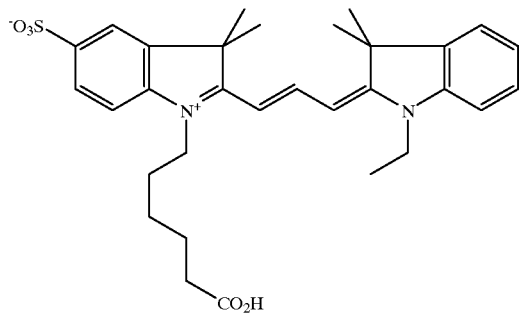

This was prepared in a standard two-step process:

1-Ethyl-2,3,3-trimethylindoleninium iodide was reacted with N,N'-diphenylformamidine and the product condensed with 1-(carboxypentyl)-2,3,3-trimethylindoleninium-5-sulphonate to give the desired parent dye after purification by chromatography.

$\lambda_{max}$(MeOH) 550 nm $\delta_H$(300 MHz; CD$_3$OD) 1.44 (3H, t, CH$_2$CH$_3$), 1.53 (2H, m), 1.71 (2H, m), 1.77 and 1.78 (each 6H, s, 2×CMe$_2$), 1.84 (2H, m) 2.31 (2H, t, CH$_2$CO$_2$H), 4.14 (2H, br t, NCH$_2$CH$_2$), 4.25 (2H, br q, NCH$_2$CH$_3$), 6.44 and 6.55 (each 1H, d, α-vinyl-H), 7.29–7.52 (4H, m, ArH), 7.57 (1H, d, ArH), 7.84–7.98 (2H, m, ArH) and 8.56 (1H, t, β-vinyl-H)

Preparation of the Protected Hydrazide

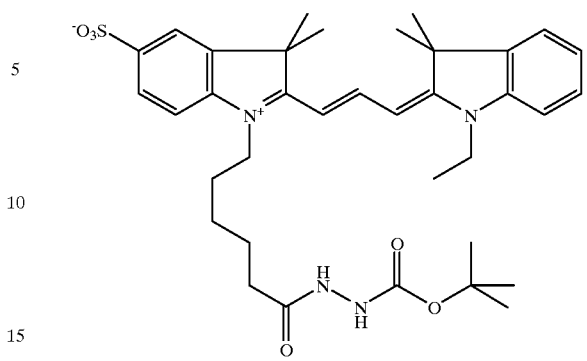

The above parent dye (110 mg), HBTU (83 mg) and tert-butyl carbazate (33 mg) were mixed with dry dimethylformamide (2 ml) and diisopropylethylamine (50 μl). After 15 min the mixture was diluted with ether and chloroform and then concentrated in vacuo and the residue partioned between chloroform and water. The organic phase was washed with dilute brine, dried (MgSO$_4$), filtered and concentrated in vacuo to give a viscous gum which was then purified by chromatography (silica; 5–25% MeOH/CHCl$_3$). Fractions containing the desired product were combined, concentrated in vacuo, redissolved in 10% MeOH/CHCl$_3$), filtered and concentrated in vacuo. The residue was then dried in vacuo at 35° C., yield 130 mg.

$\lambda_{max}$(MeOH) 550 nm $\delta_H$(300 MHz; CD$_3$OD) 1.39–1.61 (14H, m, NCH$_2$CH$_3$, $^t$-Bu and 2H), 1.66–1.94 (16H, m, 2×CMe$_2$ and 4H), 2.24 (2H, t, CH$_2$C(O)), 4.14 (2H, br t, NCH2CH$_2$), 4.24 (2H, br q, NCH$_2$CH$_3$) 6.44 and 6.55 (each 1H, d, α-vinyl-H), 7.29–7.51 (4H, m, ArH), 7.57 (1H, d, ArH), 7.85–7.98 (2H, m, ArH) and 8.56 (1H, t, β-vinyl-H)

Preparation of Hydrazide

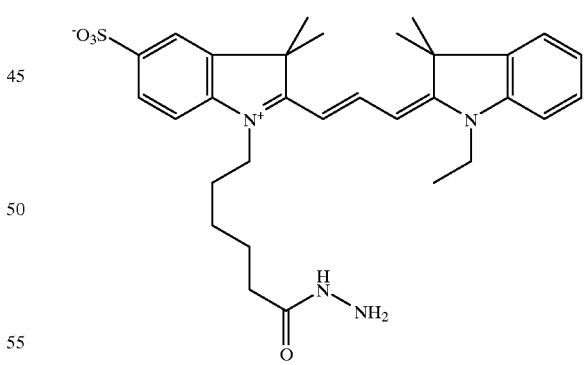

A solution of the above protected hydrazide (50 mg) in chloroform (0.5 ml) and trifluoroacetic acid (2 ml) was allowed to stand at ambient temperature for 30 min with occasional swirling. The mixture was then concentrated in vacuo and the residue reconcentrated from a 10% MeOH/CHCl$_3$ twice and then triturated with ether. The resultant solid was collected and dried in vacuo at 35° C. to afford the desired hydrazide as a brassy red-brown powder, 17 mg, which was used without any further purification.

B. Preparation of Overall +1 Cy 3 Hydrazide Preparation of Parent Dye

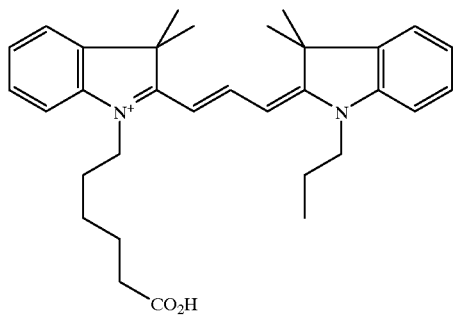

The above dye was prepared using standard procedures from 1-propyl-2,3,3-trimethylindolenium iodide, N,N'-diphenylformamidine and 1-(5-carboxypentyl)-2,3,3-trimethylindolenium bromide.

$\lambda_{max}$(MeOH) 548 nm $\delta_H$(270 MHz; DMSO-d6) 1.00 (3H, t, CH$_2$CH$_3$), 1.33–1.89, series m, 8H), 1.72 (12H, s, 2×CMe$_2$) 1.95 (2H, t, CH$_2$CO$_2$H), 4.12 (4H, m, 2×NCH$_2$), 6.56 and 6.67 (each 1H, d, α-vinyl-H), 7.20–7.39 (2H, m, ArH), 7.40–7.58 (4H, m, ArH), 7.60–7.74 (2H, m, ArH) and 8.37 (1H, t, β-vinyl-H)

Preparation of Protected Hydrazide

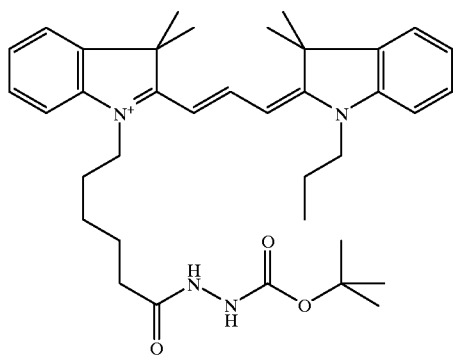

Dicyclohexylcarbodiimide (125 mg) and tert-butyl carbazate (130 mg) were added to a solution of the above parent dye (370 mg) in dichloromethane (5 ml). The resultant mixture was stirred overnight at ambient temperature, filtered and the filtrate concentrated in vacuo. The residue was triturated with ether and then purified by chromatography (silica; 5–25% MeOH/CHCl$_3$ gradient). Fractions containing the desired product were combined, filtered and concentrated in vacuo. The residue was then redissolved in 5% MeOH/dichloromethane, filtered and concentrated in vacuo. The resultant residue was then triturated repeatedly with ether until a solid was obtained which was collected and dried in vacuo at 50° C., yield 230 mg.

$\lambda_{max}$(MeOH) 548 nm $\delta_H$(300 MHz; CDC$_3$) 1.13 (3H, t, NCH$_2$CH$_2$CH$_3$), 1.43 (9H, s, $^t$-Bu), 1.60–1.05 (20H, m, 2×CMe$_2$ and 8H), 2.50 (2H, t, CH$_2$C(O)), 4.16 and 4.26 (each 2H, br t, 2×NCH2), 6.40 (1H, br s, NH), 7.05–7.47 (10H, series m, ArH and α-vinyl-H), 8.41 (1H, t, β-vinyl-H) and 9.73 (1H, br s, NH)

Preparation of the Hydrazide

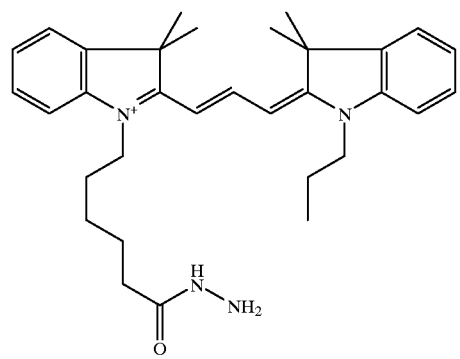

This was prepared from the above protected hydrazide (50 mg) in an analogous manner to A to yield the desired hydrazide as a sticky solid. Triturafion with ether and then concentration from a solution in dichloromethane afforded the dye as a foam which was used without any further purification.

C. Preparation of a +2 Cy3 Hydrazide

Preparation of the Parent +2 Cy3 Dye

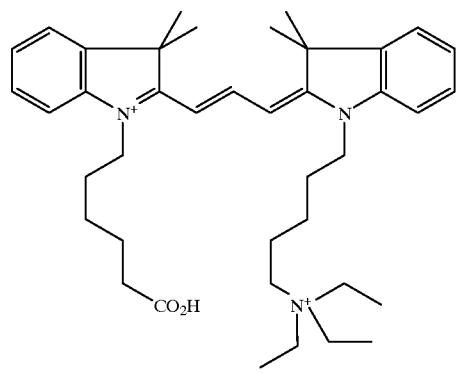

This was prepared using standard procedures from 1-(5-carboxypentyl)-2,3,3-trimethylindolenium bromide, N,N'-diphenylformamidine and 1-(3-triethylaminopropyl)-2,3,3-trimethylindolenium dibromide and was used in a partially purified form. Chromatography over alumina of small portion afforded an analytical sample.

$\lambda_{max}$(MeOH) 548 nm $\delta_H$(300 MHz; CD$_3$OD) 1.32 (9H, t, N(CH$_2$CH$_3$)$_3$), 1.40 (2H, m) 1.69–1.94 (16H, m, 2×CMe$_2$ and 4H), 2.16–2.29 (4H, m, CH$_2$C(O) and 2H), 3.39 (6H, q, N(CH$_2$CH$_3$)$_3$), 3.48 (2H, m, CH$_2$NEt$_3$), 4.18 and 4.26 (each 2H, br t, 2×ArNCH$_2$), 6.52 and 6.58 (each 1H, d, α-vinyl-H), 7.24–7.61 (8H$_1$, series m, ArH) and 8.57 (1H, t, β-vinyl-H)

Preparation of the Protected Hydrazide

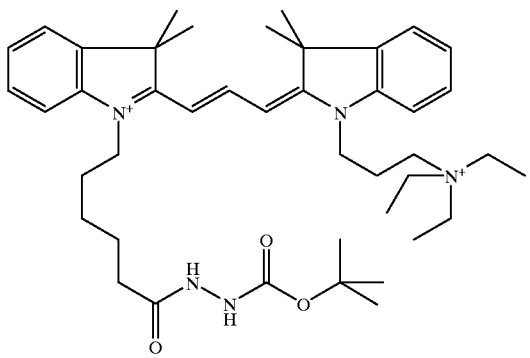

This was prepared in a similar manner to that outlined in A from tert-butyl carbazate and the parent dye acid above. Final purification was achieved by chromatography of the crude product over neutral alumina and then silica gel.

$\lambda_{max}$(MeOH) 548 nm $\delta_H$(300 MHz; CD$_3$OD) 1.32 (9H, t, N(CH$_2$CH$_3$)$_3$), 1.45 (9H, s, $^t$-Bu), 1.55 (2H, m) 1.63–1.95 (16H, m, 2×CMe$_2$ and 4H), 2.13–2.29 (4H, m, CH$_2$C(O) and 2H), 3.35 (6H, q, N(CH$_2$CH$_3$)$_3$), 3.44 (2H, m, CH$_2$NEt$_3$), 4.21 (4H, m, 2×ArNCH$_2$), 6.52 and 6.58 (each 1H, d, (α-vinyl-H), 7.23–7.63 (8H, series m, ArH) and 8.58 (1H, t, β-vinyl-H)

Preparation of the Hydrazide

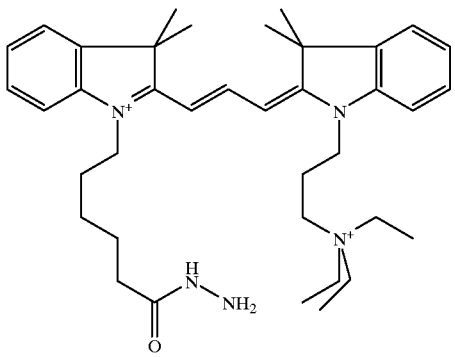

This was prepared from the protected hydrazide (50 mg), in an analogous manner to that in A, to yield a brownish-red powder (24 mg) which was used without any further purification.

Glycan Labelling Protocol

Individual glycans (~2 nmol) (Oxford Glycosciences, Abingdon Oxford UK) or 30 μg of a fetuin glycan library (Oxford Glycosciences) were dried down in a Savant Speed-Vac Concentrator. Neutral and charged cyanine dyes (Cy3) were synthesised at Amersham International plc Amersham UK. 4 μl of 1 mM Cy3 hydrazide or 1 μl of 25 mM Cy3 hydrazide in dimethyl sulphoxide (DMSO) (Sigma Chemical Co, Poole Dorset UK) were mixed with the glycan samples and incubated for 90 minutes at 42° C. Control samples contained all components including dye but no glycan. The samples were then dried down in the Savant Speed Vac Concentrator and used immediately or stored at −70° C. Dried down material was re-dissolved in 2 μl of DMSO and 38 μl of sample buffer (10% glycerol (Merck, Poole Dorset UK), 20% DMSO and 0.001% bromophenol blue (Merck)) was added. 5 μl of each sample corresponding to ~250 pmol of the individual glycan or 3.75 μg of the glycan library was added to each of two gels. One gel was used to separate net negatively charged species and the other gel to separate net positive charges.

Electrophoresis a) Separation of Glycans with Net Negative Charges

20%T/2.66%C polyacrylamide gels with a 4% stacking gel were run in a BIORAD mini-PROTEAN® II electrophoresis system at 25 Volts according to the method described by Laemmli (Nature 227: 680–685. 1970) modified by excluding SDS. The gels were pre-run for approximately 1 hour before the samples were loaded. After sample loading electrophoresis was terminated when the bromophenol blue had reached 0.25 cm from the bottom of the gel. (Pre-mixed pre-weighed acrylamide/bis was purchased from BioRad. Trizma-base was purchased from Sigma Chemical Co and glycine from Amersham Life Science Inc, Cleveland USA).

b) Separation of Glycans with Net Positive Charges

20%T/2.66%C polyacrylamide gels with a 4% stacking gel were run in a BIORAD mini-PROTEAN II electrophoresis system at 25 Volts according to 'system b' described by Thomas and Hodes (Analytical Biochemistry 118: 194–196.1981) but modified as shown below. The same gel running time was used as for separation of net negative charges. The gels were pre-run for approximately 1 hour before the samples were loaded. Histidine was from the Sigma Chemical Co. Potassium hydroxide, 3-(N-Morpholino) propane-sulphonic acid (MOPS) were from Merck.

a) Water was used in the stacking gel instead of glycerol
b) 0.1% ammonium persulphate replaced the riboflavin 5'-phosphate The results of the electrophoresis are shown in FIGS. 4 to 7 which show the fluorescent images recorded from the Molecular Fluorimager S1.

FIG. 4. Separation of glycans NA4 and NGA4.
a) Towards the positive electrode
b) Towards the negative electrode Lanes 1 to 3 (NA4) and 4 to 6 (NGA4) contain glycan labelled with a neutral, +1 and +2 dye respectively and lanes 7 to 9 are the respective controls containing neutral, +1 and +2 dye without any glycan.

FIG. 5. Separation of glycans A1 and A2.
a) Towards the positive electrode
b) Towards the negative electrode Lanes 1 to 3 (A1) and 4 to 6 (A2) contain glycan labelled with a neutral, +1 and +2 dye respectively and lanes 7 to 9 are the respective controls containing neutral, +1 and +2 dye without any glycan.

FIG. 6. Separation of neocarrahexaose oligosaccharide.
a) Towards the positive electrode
b) Towards the negative electrode Lanes 1 to 3 contain oligosaccharde labelled with a neutral, +1 and +2 dye respectively and lanes 4 to 6 are the respective controls containing neutral, +1 and +2 dye without any oligosaccharde.

FIG. 7. Separation of a glycan library.
a) Towards the positive electrode
b) Towards the negative electrode Lanes 1 to 3 contain glycans labelled with a neutral, +1 and +2 dye respectively and lanes 4 to 6 are the respective controls containing neutral, +1 and +2 dye without any glycans.

Example 1

Separation of Neutral Glycans

Glycans NA4 (2373 m.w.) and NGA4 (1724 m. w.) were labelled as described using a neutral, +1 and +2 charged fluorescent Cy3 dye derivative. Identical samples were separated using both conditions for electrophoresis described in a) and b) above.

Figure 4A:
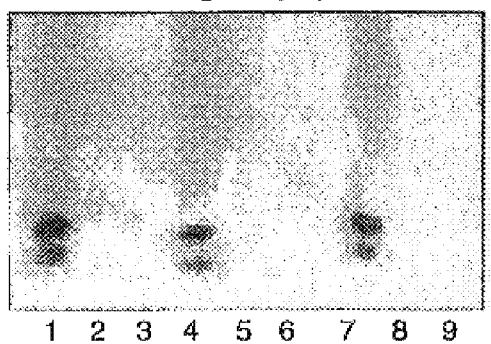
FIG. 4A shows the separation towards the positive electrode and FIG. 4B shows the separation towards the negative electrode.
Figure 4B:
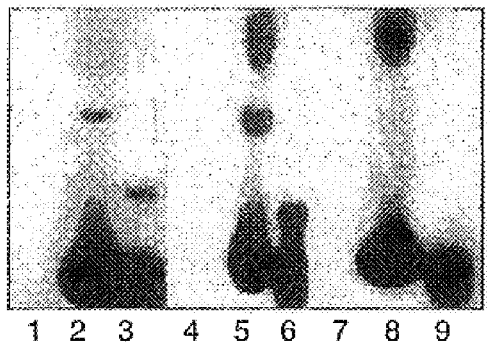

Results are shown in FIGS. 4a and 4b. Lanes 1 to 6 contain labelled glycans. Lanes 7 to 9 contain the neutral, +1 and +2 dye in the absence of glycan as negative controls. Glycans in lanes 1 and 4 were labelled with the neutral dye. Glycans in lane 2 and 5 were labelled with the +1 dye. Glycans in lanes 3 and 6 were labelled with the +2 dye.

Glycans labelled with +1 and +2 dyes were not detected when separation was made towards the positive electrode. The doublet observed in lanes 1, 4 and 7 was probably due to the presence of the unconverted acid form of the Cy3 dye. Bands representing free dye were visible in the lanes containing glycans labelled with +1 and +2 when separation was made towards the negative electrode.

There was no difference between the control lanes and the labelled glycan lanes when electrophoresis was performed towards the positive electrode confirming that the glycans were not negatively charged to begin with. If the labelled glycans had been negatively charge a band would have been visible in lane 1.

The results from the separation towards the negative electrode show an additional band in lanes 2 and 3 and 5 and 6 when compared to the negative controls. No band representing labelled glycan was visible in lanes 1 and 4. A neutral dye will not confer charge to a neutral glycan. In the absence of a net charge a labelled glycan will not enter the gel. A band is visible in lanes 2 and 5 because the glycan has one net positive charge. Glycans in lanes 3 and 6 have gained two positive charges as a result of labelling and therefore have migrated further into the gel. Glycan NGA4 has a lower molecular weight than NA4 and this is reflected by their relative mobility.

Neutral glycans will only enter the gel towards the negative cathode after they have been labelled with a positively charged dye. The relative mobility is affected by molecular weight and overall charge.

Example 2
Separation of Negatively Charged Glycans

Glycans A1 and A2 contain 1 and 2 sialic acid groups respectively. Each glycan was labelled with a neutral, +1 and +2 charged fluorescent Cy3 dye derivative. The labelled samples were separated using both sets of conditions for electrophoresis described in a) and b) above.

Figure 5A:
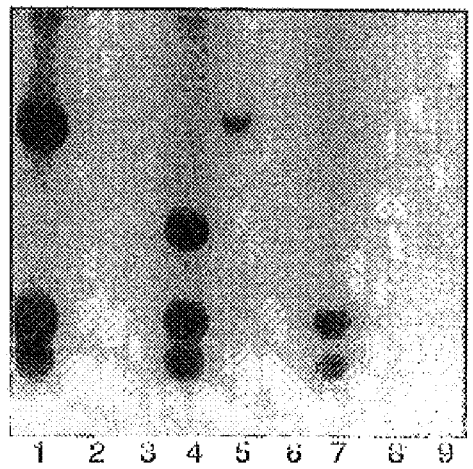
FIG. 5A shows the separation towards the positive electrode and FIG. 5B shows the separation towards the negative electrode.
Figure 5B:
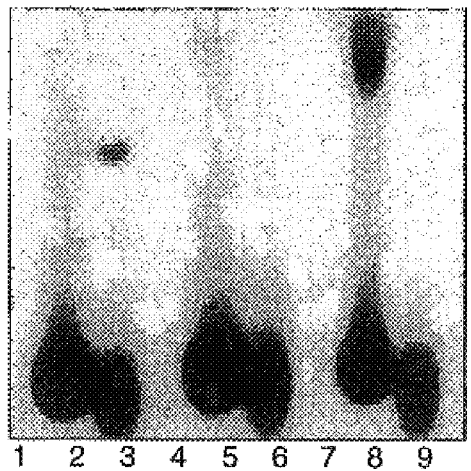

The results are shown in FIGS. 5a and 5b. Lanes 1 to 6 contain labelled glycans. Lanes 7–9 contain the neutral, +1 and +2 dye in the absence of glycan as negative controls. Lanes 1, 2 and 3 contain A1 glycan labelled with neutral, +1 and +2 dye and lanes 4, 5 and 6 contain A2 glycan labelled with neutral, +1 and +2 dye.

When the labelled glycans were separated towards the positive electrode a single band was observed in lane 1. When the labelled glycans were separated towards the negative electrode no band was present in lane 1. These data are predicted if Glycan A1 has a net −1 charge after labelling with a neutral dye.

No bands representing labelled glycans were observed when separated towards the positive electrode or towards the negative in lane 2. The absence of bands in these lanes can be predicted where a single positively charged dye countered the negative charge on the native A1 glycan.

When the labelled glycans were separated towards the positive electrode no bands were observed in lane 3. When the labelled glycans were separated towards the negative electrode a single band was present in lane 3. These data are predicted if a dye bearing a net +2 charge is used to label the native A1 glycan bearing a single negative charge. In this case, the labelled glycan would have a net +1 charge and would move toward the negative electrode.

When the labelled glycans were separated towards the positive electrode a band was observed in lane 4. When the labelled glycans were separated towards the negative electrode no bands were observed in lane 4. These data are predicted if a neutral dye was used to label Glycan A2 because the native form of Glycan A2 has a net −2 charge. Furthermore, the band observed in lane 5 is predicted when A2 is labelled with a dye bearing a net −1 charge and separated towards the positive electrode because the −2 glycan and +1 labelling dye result in a net −1 charge after labelling. The labelled A2 glycan with a single negative charge has migrated a shorter distance into the gel than the labelled glycan observed in lane 4. No bands are predicted or observed in lane 6 under any conditions assuming that the glycan labelled with the dye bearing a +2 charge is neutral.

Fluorescent dye labelled A1 and A2 glycans gave the predicted banding when separated toward either the positive or negative electrode during electrophoresis. The banding pattern can be used to infer the charge on the native glycan.

Example 3
Separation of an Oligosaccharide Neocarrahexaose Which Has a Net 3− Charge The neocarrahexaose oligosaccharide tri-sulphate (overall charge −3) was purchased from Dextra Laboratories, Reading UK. The oligosaccharide was labelled with a neutral, +1 and +2 charged fluorescent is Cy3 derivative. The labelled samples were separated using both sets of conditions for electrophoresis described in a) and b) above.

Figure 6A:
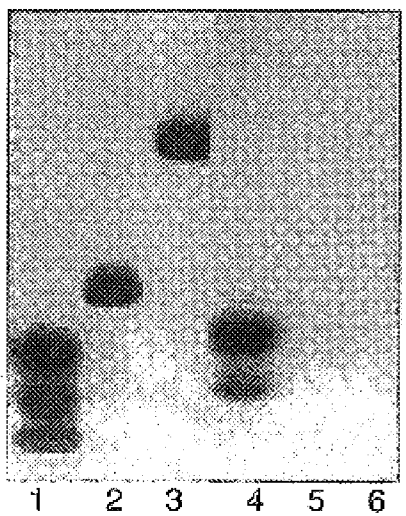
FIG. 6A shows the separation towards the positive electrode and FIG. 6B shows the separation towards the negative electrode.
Figure 6B:

Results are shown in FIGS. 6a and 6b. Lanes 1 to 3 contain labelled oligosaccharides. Lanes 4 to 6 contain the neutral, +1 and +2 dye in the absence of oligosaccharide as negative controls. Oligosaccharide in lane 1,2 and 3 were labelled with the neutral dye, dye bearing a +1 charge and dye bearing a +2 charge respectively.

Bands representing labelled oligosaccharide were observed in lanes 1, 2 and 3 when separated towards the positive electrode but no bands were observed in lanes 1, 2 and 3 when labelled products were separated or towards the negative electrode. A band is predicted in lanes 1, 2 and 3 assuming that there is a −3, −2 and −1 charge respectively on the labelled oligosaccharides. The mobility of the labelled oligosaccharide would be greatest when it had a −3 overall charge as shown in lane 1 when separated toward the positive electrode. Although three bands were present in lane 1 two are present in lane four therefore the additional band is the labelled oligosaccharide.

Neocarrahexaose oligosaccharide tri-sulphate gave the expected banding patterns when labelled with a neutral or a series of positively charged fluorescent dyes. The charge on the oligosaccharide could be predicted as −3 or greater from the banding pattern in this experiment.

Example 4
Separation of a Glycan Library

The glycans in this library were released from the native glycoprotein by hydrazinolysis. The released glycans were negatively charged; charges ranged from −1 to −4. The glycans were labelled with a neutral, +1 and +2 charged fluorescent Cy3 dye derivative. The labelled samples were separated using both sets of conditions for electrophoresis described in a) and b) above.

Figure 7A:
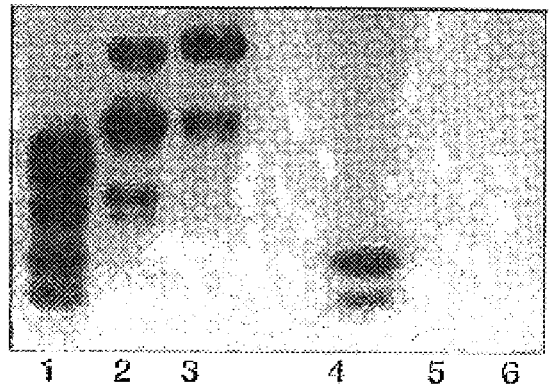
FIG. 7A shows the separation towards the positive electrode and FIG. 7B shows the separation towards the negative electrode.
Figure 7B:
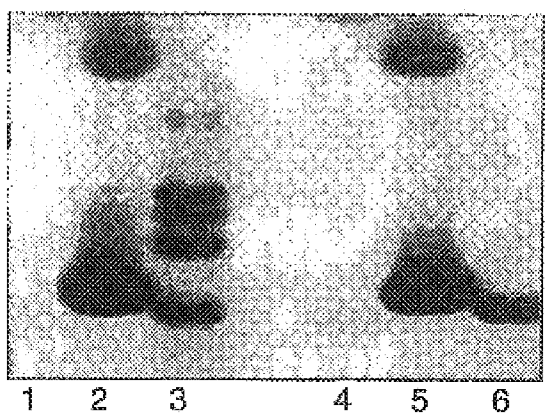

The results are shown in FIGS. 7a and 7b. Lanes 1 to 3 contain the labelled glycans. Lanes 4 to 6 contain the neutral, +1 and +2 dye in the absence of glycan as negative controls.

Lane 1, 2 and 3 contain glycans labelled with the neutral dye, +1 dye and the +2 dye.

When the labelled glycans were separated towards the positive electrode bands were observed in lane 1. When the labelled glycans were separated towards the negative electrode no bands were present in lane 1. These data are predicted if the glycans are labelled with a neutral dye.

When glycans were labelled with a dye bearing a single positive charge and separated towards the positive electrode, the banding pattern in Lane 2 reflected the exclusion of those glycans which originally had a −1 charge. Similarly. the banding pattern in Lane 3 reflected the exclusion of those glycans which originally had a −1 or a −2 charge. The predicted banding pattern is seen with progressively less glycans entering the gel.

When labelled glycans were separated towards the negative electrode bands were observed only in lane 3. Bands are predicted in lane 3 if the unlabelled glycan had a −1 charge and then gained an overall +1 charge after labelling with a dye bearing a +2 charge.

The charge on a library of glycans released from protein by chemical cleavage and labelled with neutral or positively charged fluorescent dyes can be predicted for those entering the gel from the banding pattern after electrophoresis.

Example 5
Separation of Glycans by Iso-electric Focusing Followed by Second Dimensional Gel Electrophoresis Glycan A3 contains 3 sialic acid groups and therefore has three negative charges. The glycan was labelled with a +2 charged fluorescent Cy3 dye derivative. The overall net charge on the molecule was −1. An immobilised pH gradient strip pH 3 to 10 NL (Pharmacia Biotech, Uppsala Sweden) was re-hydrated in a cassette of water containing 0.52% pH 3–10 Pharmalytes (Pharmacia Biotech) for 2 hours. 10 µl (500 ng) of labelled A3 was loaded on to the Multiphor II system from Pharmacia Biotech. The strip was focused at 100 volts for 1 hour followed by 300 volts for 2 hours and finally at 2000 volts for a total of 3300 volt hours.

The IEF strip was used to carry out a second dimension separation perpendicular to the first. The IEF strip was separated using the conditions for electrophoresis described in a) with the following modifications: A Hoefer system 18×16 cm gel was used. The strip was loaded on to a 1 mm thick gel containing 12 cm length of resolving gel and 2 cm stacking gel. A 2 cm gap at the top of the gel was filled with LMP agarose heated to 70° C. The IEF strip was loaded into the heated agarose which was allowed to set for a short time. The gel was run for 3 hours at 25 mA constant current towards the cathode allowing separation of net negative charges.

The IEF result was: A single band corresponding to the labelled A3 glycan was seen in the acidic region of the gel.

The second dimension result was: Labelled glycan from the acidic region of the IEF gel had migrated into the polyacrylamide gel.

Table 1

List of Fluorescent Labelling Reagents for Application in the Methods Set Out in the Invention
2-acetamido4-trimethylammoniobimanylmercaptobutyric acid
2-aminoacridone
2-aminopyridine
7-(arginylamino)-4-methylcoumarin
7-(arginylarginylamino)-4-methylcoumarin
7-(arginylarginylarginylamino)-4-methylcoumarin
7-(arginylglycylarginylarginylamino)-4-methylcoumarin
7-(lysylamino)-4-methylcoumarin
7-(lysyllysylamino)-4-methylcoumarin
7-(lysyllysyllysylamino)-4methylcoumarin
7-amino-4-methylcoumarin
aminofluorescein
aminorhodamine
cyanine dyes
coumarin 120
coumarin 120
coumarin 151
dansylcadaverine
ethidium bromide
lucifer yellow
lucifer yellow biotinylated
Nile blue A
proflavine and monoaminoderivatives
propidium bromide
rhodamine 101 methyl ester
rhodamine 123
2-aminobenzoic acid Table 2

List of Fluorescent Labelling Reagents for Use with Hydrazine Cleaved Carbohydrate Substances
5-((2-aminoethyl)thioureidyl)fluorescein
4'-(aminomethyl)fluorescein, hydrochloride
5-(aminomethyl)fluorescein, hydrochloride
7-amino4-methyicoumarin
1-aminomethylpyrene, hydrochloride
8-aminonaphthalene-1,3,6-trisilfonic acid, disodium salt (ANTS)
5-(and 6)-((N-%aminopentyl)amino)carbonyl) tetramethylrhodamine (tetramethylrhodamine cadaverine)
N-(5-aminopentyl)-4-amino-3,6-disulfo-1,8-naphthalimide, dipotassium salt (Lucifer Yellow cadaverine)
5-((5-aminopentylthioureidyl)eosin, hydrochloride (eosin cadaverine)
5-((5-aminopentyl)thioureidyl)fluorescein (fluorescein cadaverine)
6-aminoquinoline
4', 5'-bis-(aminomethyl)fluorescein, dihydrochloride
5-(((2-(carbohydrazino)methyl)thio)acetyl)aminoeosin
5-(((2-(carbohydrazino)methyl)thio)acetyl) aminofluorescein
Cascade Blue cadaverine, trisodium salt
Cascade Blue ethylenediamine, trisodium salt
Cascade Blue hyrazide, tripotassium salt
Cascade Blue hydrazide, trisodium salt
1,2-diamino-4,5-dimethyoxybenzene, monohydrochloride (DDB)
7-diethylaminocoumarin-3-carbohydrazide (DCCH)
4,4-difluoro-5,7-dimethyl-4-bora-3a,4a-diaza-s-indacene-3-propionylethylenediamine, hydrochloride (BOOIPY®FL C₃ EDA)
4,4-difluoro-5,7-dimethy)-4-bora-3a,4a-diaza-s-indacene-3-propionyl hydrazide
4,4-difluoro-5,7-diphenyl-4-bora-3a,4a-diaza-s-indacene-3-propionylethylenediamine
4,4-difluoro-5,7-diphenyl-4-bora-3a,4a-diaza-s-indacene-3-propionyl hydrazide (BODIPY® 530/550 C₃ hydrazide)
4,4-difluoro-1,3,5,7-tetramethy-bora-3a,4a-diaza-s-indacene-3-propionyl hydrazide (BODIPY® 493/503 C₃ hydrazide)

Table 2 (continued)

5-dimethylaminonaphthalene-1-(N-(2-aminoethyl) sulfonamide (dansyl ethylenediamine)

5-dimethylaminonaphthalene-1-(N-(2-aminopentyl) sulfonamide (dansyl cadaverine)
5-dimethylaminonaphthalene-1-sulfonyl hydrazine (dansyl hydrazine)
N-ε-(5-dimethylaminonaphthalene-1-sulfonyl-1-lysine (dansyl lysine)
N-(3-((2,4-dinitrophenyl)amino)propyl)-N-(3-aminopropyl) methylamine, dihydrochloride
eosin-5-thiosemicarbazide
erythrosin-5-thiosemicarbazide
1-ethyl-3-(3-dimethylaminopropyl)carbodiimide, hydrochloride (EDAC)
fluorescein-5-thiosemicarbazide
Lissamine™ rhodamine B sulfonyl hydrazine
Lissamine™ rhodamine B sulfonylethylenediamine
Lucifer yellow CH, ammonium salt
Lucifer yellow CH, lithium salt
Lucifer yellow CH, potassium salt
p-nitrophenyl 3-diazopyruvate
1-pyrenebutyrylhydrazine
succinimidyl p-formylbenzoate (SFB)
succinimidyl p-formylphenoxyacetate (SFPA)
Texas Red® hydrazide
Texas Red® sulfonylcadaverine
2-aminobenzoic acid
2-aminobenzoic acid amide

What is claimed is:

1. A method of separating carbohydrate substances, comprising contacting the carbohydrate substances with two or more different fluorescent labeling reagents to bind said labeling reagents to said carbohydrate substances, wherein each of said two or more reagents comprise a reactive group capable of binding to a carbohydrate, and wherein each reagent carries a positive charge which is different from that carried by any other of the different reagents, and separating the carbohydrate substances by virtue of the different positive charges on the labeling reagents.

2. A method of separating carbohydrate substances that have been cleaved or released by hydrazine, comprising the step of labeling the carbohydrate substances by binding two or more different fluorescent labeling reagents to said carbohydrate substances, wherein each said labeling reagent has a reactive group capable of binding to a carbohydrate, and wherein each reagent carries a positive charge which is different from that carried by any other of the different reagents, and separating the carbohydrate substances by virtue of the different positive charges on the labeling reagents.

3. A method as claimed in claim 1 or claim 2, wherein said separation is effected by applying the labeled carbohydrate substances to an electrophoresis matrix and performing electrophoresis to cause differential migration of differently labeled carbohydrate substances.

4. A method as claimed in claim 3, wherein said electrophoresis is performed to cause differential migration of differently labeled carbohydrate species in a cathodic and/or in an anodic direction.

5. A method according to claim 3 further comprising imaging the labeled carbohydrate substance following said electrophoresis.

6. A method as claimed in claim 1 or claim 2, wherein separation of differently labeled carbohydrate substances is effected by isoelectric focusing in a pH gradient.

7. A method as claimed in claim 6, wherein the pH gradient is generated by carrier ampholytes and/or is immobilized.

8. A method as claimed in claim 1 or claim 2, wherein the labeling reagents comprise a positive charge conferred by a tertiary amine group, secondary amino group, quaternary amine, guanidinium, imidazole or pyridinium group.

9. A method as claimed in claim 1 or claim 2, wherein the fluorescent labeling reagents comprise a cyanine dye.

10. A method as claimed in claim 1 or 2, wherein the reactive group capable of binding to a carbohydrate is primary amine, hydrazine, aminoxy, secondary or pyrazolone.

11. A method as claimed in claim 1 or claim 2, wherein separation of differently labeled carbohydrate substances comprises: a first step of isoelectric focusing in a pH gradient in which the labeled carbohydrates migrate in a first direction; and a second step of gel electrophoresis, in which the labeled carbohydrate substances migrate in a perpendicular direction to their migration in the first step.

12. A method of separating carbohydrate substances comprising labeling the carbohydrate substances by binding two or more different fluorescent labeling reagents to aliquots of said carbohydrate substances, wherein each of said reagents has a reactive group capable of binding to a carbohydrate, and wherein each reagent carries a positive charge which is different from that carried by any other of the different reagents, and separating the carbohydrate substances by virtue of the different positive charges on the labeling reagents.

13. A method as claimed in claim 12, wherein the aliquots are mixed before separation of differently labeled carbohydrate substances.

* * * * *